US012577189B2

(12) United States Patent
Lee et al.

(10) Patent No.: US 12,577,189 B2
(45) Date of Patent: Mar. 17, 2026

(54) REMOVAL OF ACETALS FROM PROCESS STREAMS

(71) Applicant: Celanese International Corporation, Irving, TX (US)

(72) Inventors: David Lee, Houston, TX (US); Yaw-Hwa Liu, Missouri City, TX (US); Ronald D. Shaver, Houston, TX (US)

(73) Assignee: Celanese International Corporation, Irving, TX (US)

( * ) Notice: Subject to any disclaimer, the term of this patent is extended or adjusted under 35 U.S.C. 154(b) by 593 days.

(21) Appl. No.: 17/928,569

(22) PCT Filed: Jun. 3, 2021

(86) PCT No.: PCT/US2021/035689
§ 371 (c)(1),
(2) Date: Nov. 29, 2022

(87) PCT Pub. No.: WO2021/247855
PCT Pub. Date: Dec. 9, 2021

(65) Prior Publication Data
US 2023/0202955 A1     Jun. 29, 2023

Related U.S. Application Data

(60) Provisional application No. 63/034,086, filed on Jun. 3, 2020.

(51) Int. Cl.
*C07C 45/83* (2006.01)

(52) U.S. Cl.
CPC .................................... *C07C 45/83* (2013.01)

(58) Field of Classification Search
None
See application file for complete search history.

(56) References Cited

U.S. PATENT DOCUMENTS

| | | | |
|---|---|---|---|
| 4,908,477 | A | 3/1990 | Hartmann et al. |
| 2005/0197509 | A1 | 9/2005 | Picard et al. |
| 2018/0118651 | A1 | 5/2018 | Shimizu et al. |
| 2020/0140365 | A1 | 5/2020 | Shaver |

FOREIGN PATENT DOCUMENTS

| | | |
|---|---|---|
| CN | 1926089 A | 3/2007 |
| CN | 107709279 A | 2/2018 |
| JP | 04266843 A | 9/1992 |
| JP | 05320086 A | 12/1993 |
| JP | 2005515227 A | 5/2005 |
| JP | 2011502145 A | 1/2011 |
| TW | 364901 B | 7/1999 |
| WO | 2016194850 A1 | 12/2016 |

OTHER PUBLICATIONS

International Search Report and Written Opinion for PCT/US2021/035689 mailed Sep. 16, 2021, all pages.
Notification of the First Office Action for China Appln No. 202180040043.0 dated May 6, 2024, 18 pages.
CN202180040043.0, "Office Action", Jan. 7, 2025, 14 pages.
JP2022-574394, "Office Action", Dec. 18, 2024, 8 pages.
International Preliminary Report on Patentability for PCT/US2021/035689 issued Dec. 6, 2022, 8 pages.
Application No. TW110120146, Office Action, Mailed on Nov. 1, 2024, 13 pages.
Application No. CN202180040043.0, Office Action, Mailed On Jul. 1, 2025, 19 pages.
MYPI2022006776, "Substantive Examination Adverse Report", Jun. 13, 2025, 5 pages.
Application No. SA522441549, Office Action, Mailed On Jun. 2, 2025, 10 pages.
Application No. SG11202260759Y, Written Opinion, Mailed On Jun. 13, 2025, 7 pages.
Application No. TW110120146, Notice of Decision to Grant, Mailed On May 29, 2025, 7 pages.

*Primary Examiner* — Ana Z Muresan

(74) *Attorney, Agent, or Firm* — Kilpatrick Townsend & Stockton LLP

(57) ABSTRACT

A process for producing acetic acid is provided that is capable of lowering acetaldehyde mass composition in acetic acid. The process for producing acetic acid according to the present invention comprises at least one distillation step that satisfies the following operating conditions (i) temperature in a lower portion of the distillation column is not less than 40° C.; (ii) water mass composition in the lower stream is not less than 0.3 wt. %; or (iii) acetic acid mass composition in the lower stream on weight percentage basis is greater than the acetic acid mass composition in the first mixture; wherein the methanol mass composition in the first mixture is less than or equal to 2 wt. %.

20 Claims, 5 Drawing Sheets

REMOVAL OF ACETALS FROM PROCESS STREAMS

This application is a U.S. National Phase of PCT/US2021/035689, filed Jun. 3, 2021, entitled "REMOVAL OF ACETALS FROM PROCESS STREAMS," which claims priority to U.S. Provisional Application No. 63/034,086, filed on Jun. 3, 2020, the entire contents of which are incorporated herein by reference for all purposes.

FIELD OF THE INVENTION

The present disclosure relates generally to improved processes for producing high quality acetic acid. In particular, the process relates to lowering acetaldehyde, on a mass basis, by distilling a first mixture containing at least methanol, water, $C_1$-$C_{12}$ alkyl iodides, and at least one permanganate reducing compounds (e.g., acetaldehyde) at specific operating conditions in a distillation column to control acetal formation. The operating conditions in the distillation column inhibit or reduce acetal in the distillation column for efficient separation of acetaldehyde from the first mixture.

BACKGROUND OF THE INVENTION

The methanol carbonylation process is a suitable industrial synthesis process for producing acetic acid. Despite the high yields of acetic acid, the process is known to generate impurities resulting in low purity acetic acid. One such impurity that has received considerable attention is acetaldehyde because of the relevant difficulty in removal, acetaldehyde is a precursor to several other impurities, and the impact on purity of acetic acid. For example acetaldehyde has a close boiling point to an effective catalyst promoter, which makes simple distillation insufficient. To overcome these insufficiencies, several proposals have been to remove acetaldehyde by alkane or water extraction, or by reaction with amino compounds, oxygen-containing gases, and hydroxyl compounds. Unfortunately, despite the use of these treatments, acetaldehyde continues to be challenge in obtaining high purity acetic acid. Further, formation of acetaldehyde derived impurities reduces the efficiency when removing acetaldehyde.

In acetic acid production process, acetaldehyde by-products are produced in the acetic acid production process. For example, the reaction mixture contains small amounts of by-products (impurities), for example, acetaldehyde by-products (e.g., butyraldehyde, crotonaldehyde, 2-ethylcrotonaldehyde, and an aldol condensation product thereof), an organic iodide (e.g., a $C_{2-12}$ alkyl iodide such as ethyl iodide, butyl iodide, or hexyl iodide), and others. These impurities result in low quality acetic acid. Conventional process use distillation columns and treatment units to further improve the production of high quality acetic acid. While such treatments are beneficial for removing certain types of impurities, these columns and units are limited with respect to some impurities.

Therefore, conventional processes do not increase the efficiency of acetaldehyde removal in the distillation column because acetaldehyde is not efficiently separated into an overhead. Although existing carbonylation processes are highly efficient, further improvements for the recovery of high-purity acetic acid in a safe and efficient manner continue to be desirable.

SUMMARY OF THE INVENTION

In some embodiments, the present invention provides a process for producing acetic acid by reduction of acetaldehyde derived impurities, including 1,1-dimethoxyethane.

In some embodiments, the present invention provides a process for purifying acetic acid by utilizing overhead extraction of a permanganate reducing compound (PRC), such as but not limited to acetaldehyde, from a stream comprising methanol, acetaldehyde, water, and one or more $C_1$-$C_{12}$ alkyl iodides.

In some embodiments, the present invention provides a process for producing acetic acid while controlling and/or regulating the mass composition of methanol in a distillation column to efficiently separate acetaldehyde.

As used herein the terms "mass composition" or "concentration" refers to the mass fraction of substance to the total mass and is generally expressed in wt % or % by weight, unless indicated otherwise.

In some embodiments, the present invention provides a process for efficiently separating PRC's and methyl iodide from each other by extractive distillation of PRC's in the coexistence of methanol, acetaldehyde, water, and one or more $C_1$-$C_{12}$ alkyl iodides, and a process for producing acetic acid.

In some embodiments, the present invention provides a process for efficiently separating PRC's and methyl iodide from each other by distillation of PRC's in the coexistence of methanol, acetaldehyde, water, and one or more $C_1$-$C_{12}$ alkyl iodides, without the supply of additional water to the distillation column, and a process for producing acetic acid.

In some embodiments, the present invention provides a process for efficiently separating PRC's and methyl iodide from each other by extractive distillation of PRC's wherein the distillation column is operated under conditions to prevent formation of 1,1-dimethoxyethane.

In one embodiment there is disclosed a process for separating acetaldehyde from a first mixture comprising acetaldehyde, one or more $C_1$-$C_{12}$ alkyl iodides (methyl iodide), water, and methanol, the process comprising the steps of distilling the first mixture in a distillation column to form at least two streams selected from the group consisting of an overhead stream, sidecut stream, and lower stream, wherein either the overhead stream or sidecut stream are withdrawn as a second mixture; separating acetaldehyde from the second mixture; and controlling the 1,1-dimethoxyethane mass composition in the lower stream to less than or equal to 0.03 wt. % by operating the distillation column under at least one of the following conditions (i) to (iii): (i) temperature in a lower portion of the distillation column is not less than 40° C.; (ii) water mass composition in the lower stream is not less than 0.3 wt. %; or (iii) acetic acid mass composition in the lower stream on weight percentage basis is greater than the acetic acid mass composition in the first mixture; and wherein the methanol mass composition in the first mixture is less than or equal to 2 wt. %.

In one embodiment, there is provided a process for separating acetaldehyde from a first mixture comprising acetaldehyde, one or more $C_1$-$C_{12}$ alkyl iodides, water, and methanol, the process comprising the steps of distilling the first mixture in a distillation column to form at least two streams selected from the group consisting of an overhead stream, sidecut stream, and lower stream, wherein the sidecut stream is withdrawn as a second mixture, separating the second mixture into an aqueous stream comprising acetaldehyde or an organic stream comprising the one or more $C_1$-$C_{12}$ alkyl iodides, and controlling the 1,1-dimethoxyethane mass composition in the lower stream to less than or equal to 0.03 wt. % by operating the distillation column under at least one of the following conditions (i) to (iii): (i) temperature in a lower portion of the distillation column is not less than 40° C.; (ii) water mass composition in the lower stream is not less than 0.3 wt. %; or (iii) acetic acid mass composition in the lower stream on weight percentage basis is greater than the acetic acid mass composition in the first mixture; and wherein the methanol mass composition in the first mixture is less than or equal to 2 wt. %.

BRIEF DESCRIPTION OF THE DRAWINGS

The present invention will be better understood in view of the appended non-limiting figures, wherein.

Figure 1:
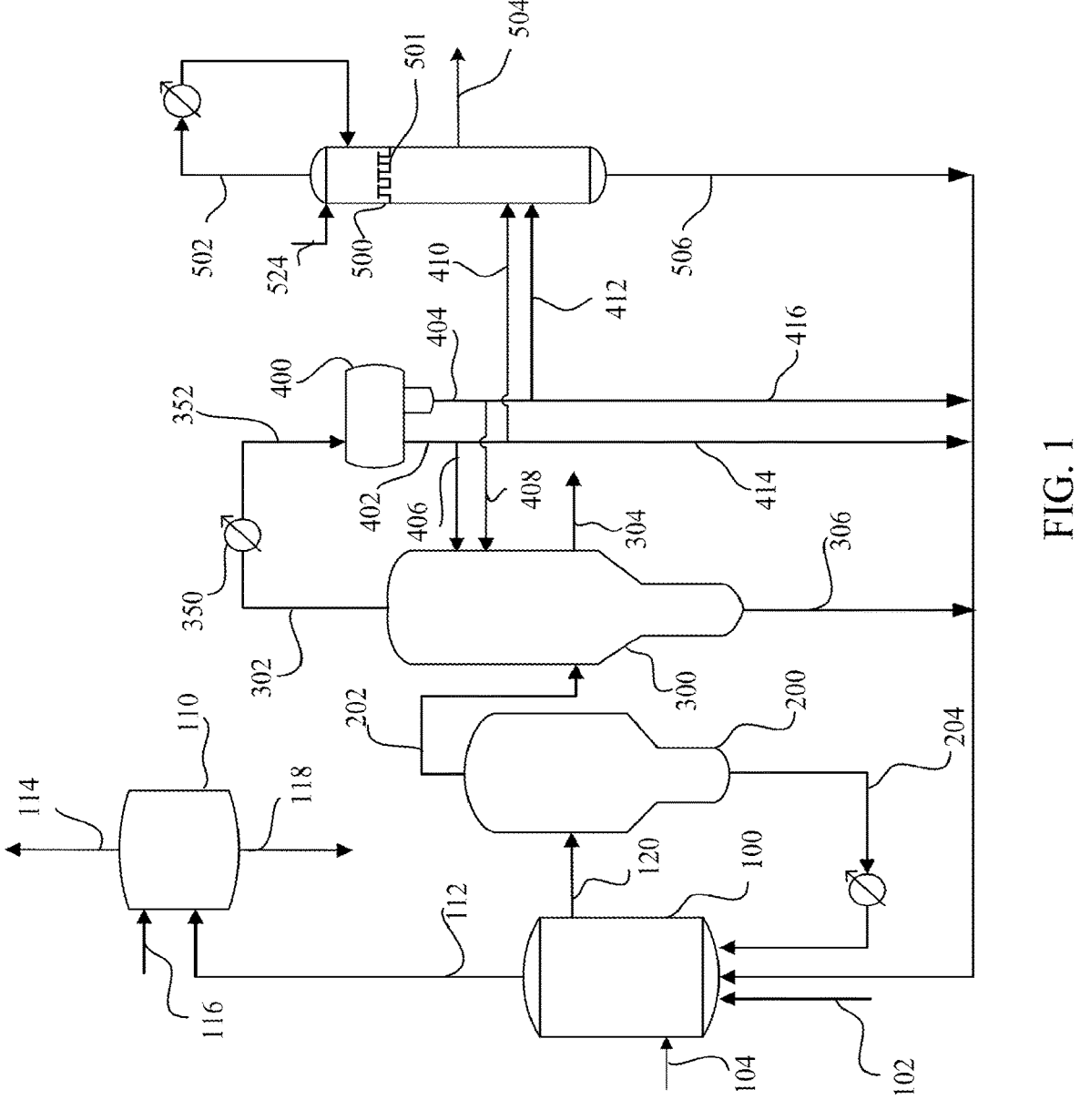
FIG. 1 illustrates a schematic flow diagram of acetic acid production in accordance with some embodiments of the present invention.

At the outset, it should be noted that in the development of any such actual embodiment, numerous implementation-specific decisions must be made to achieve the developer's specific goals, such as compliance with system related and business related constraints, which will vary from one implementation to another. In addition, the processes disclosed herein can also comprise components other than those cited or specifically referred to, as is apparent to one having average or reasonable skill in the art.

As is evident from the figures and text presented herein, a variety of embodiments are contemplated.

DETAILED DESCRIPTION OF EMBODIMENTS

The process for producing acetic acid according to the present invention comprises at least one distillation step that satisfies at least one of the following operating conditions: (i) temperature in a lower portion of the distillation column is not less than 40° C.; (ii) a water mass composition in the lower stream is not less than 0.3 wt. %; and/or (iii) acetic acid mass composition in the lower stream, based on the total weight of the lower stream, is greater than the acetic acid mass composition in the first mixture. In the distillation step that satisfies such operating conditions, acetal and/or hemiacetal formation in the lower portion of a distillation column is efficiently inhibited and/or reduced. Without being bound by theory, it is believed that the equilibrium (reversible) reaction is shifted under the operating conditions described above to reduce acetalization of acetaldehyde to acetal and/or hemiacetal. A distillation step that satisfies the aforementioned operating conditions may inhibit or reduce acetal and/or hemiacetal formation for efficient separation of acetaldehyde and prevents methanol formation such that the mass composition of methanol in the lower portion of the distillation column is less than or equal to 2 wt. %.

According to the present invention, a process for producing acetic acid including a distillation step that satisfies particular operating conditions can inhibit or reduce acetal and/or hemiacetal formation in a lower portion of a distillation column. Therefore, the acetaldehyde that is distributed to the lower portion of the distillation column with the acetal can be efficiently separated in a distillation step to reduce the acetal mass composition (and consequently lower acetaldehyde mass composition) in the produced acetic acid, or a bottom fraction having a lower mass composition of acetaldehyde can be recycled to the reactor.

It was surprisingly found that the formation of 1,1-dimethoxyethane can be inhibited or reduced in the lower stream of the distillation column at specific operating conditions in the distillation column. The inventors found that by operating a distillation column that satisfies at least one of the following conditions can inhibit acetal formation in a lower portion of the distillation column: (i) temperature in a lower portion of the distillation column is not less than 40° C.; (ii) water mass composition in the lower stream is not less than 0.3 wt. %; or (iii) acetic acid mass composition in the lower stream on weight percentage basis is greater than the acetic acid mass composition in the first mixture. Under these operating conditions, the methanol mass composition is inhibited in the lower portion of the distillation column and is less than or equal to 2 wt. %.

The inventors of the present invention achieved the above improved processes for producing high-purity acetic acid by conducting extensive studies to discover that acetal is formed in a distillation step at specific operating conditions and when high amounts of methanol are present with acetaldehyde. It was found that at a higher methanol amounts, more acetal is formed in the lower portion of a distillation column. As a result acetaldehyde is transformed or converted by a reversible reaction to an acetal and exits the liquid stream in the bottom. Due to the reversible nature, acetal can be reconverted by to acetaldehyde upon recycling. This limits the ability to remove acetaldehyde in the present of methanol due to the trapping in the acetal form. As a result, acetaldehyde in the mixture to the distillation column distributes to a lower portion of the distillation column in the form of an acetal to produce a second mixture that is easily converted back through the reversible reaction, thereby preventing efficient separation of acetaldehyde in the distillation column.

In particular, the inventors have found that under certain operating conditions in the distillation column, 1,1-dimethoxyethane, a higher-boiling point component (e.g., 64° C.), is formed in the lower part of the distillation column and acetaldehyde removal becomes limited with the increased amount of 1,1-dimethoxyethane mass composition, thereby leading to a low-quality acetic acid product.

Accordingly, the inventors have conducted further studies and found that a distillation column can be operated to inhibit or reduce acetal formation by maintaining a high temperature, a minimum water amount, and/or high acetic acid amount in the lower portion of a distillation column. In a distillation column that satisfies these conditions, lower amounts of 1,1-dimethoxyethane are formed in the lower portion of the distillation column. Lower amounts of 1,1-dimethoxyethane improve the removal of acetaldehyde. By reducing the amounts of 1,1-dimethoxyethane in the lower stream, there is less available acetaldehyde which may be transformed through the reversible reaction. Thus, acetaldehyde can be efficiently separated by, for example, water extractive distillation.

During methanol carbonylation, acetaldehyde or byproducts of acetaldehyde present in the mixture to the distillation column may undergo acetalization to produce acetals and/or hemiacetals. The acetalization of acetaldehyde (AcH) to acetal (e.g., 1,1-dimethoxyethane) is a two-step acid catalyzed reaction in methanol carbonylation system. The first step the acetaldehyde reacts with methanol to form the hemiacetal. The second step the hemiacetal reacts with methanol to yield the acetal, 1,1-dimethoxyethane, and water. The overall reaction is shown in Formula I as:

$$CH_3CHO + 2CH_3OH \rightleftharpoons (CH_3O)_2CHCH_3 + H_2O \qquad \text{Formula 1}$$

The acetalization of acetaldehyde (AcH) to acetal (e.g., 1,1-dimethoxyethane) is an equilibrium (reversible) reaction as shown:

$$Keq = \frac{[Acetal][H_2O]}{[AcH][CH_3OH]^2}$$

Under certain operating conditions in the distillation column (e.g., low temperature, low water conditions, and/or low acetic acid mass composition in the lower portion of a distillation column), the equilibrium reaction may favor acetalization of acetaldehyde. Further, the acetalization reaction may be further catalyzed in the presence of mineral acids or carboxylic acids such as acetic acid. Thus, acetal mass compositions may increase in the distillation column during the recovery of acetic acid from a mixture causing more acetaldehyde to distribute to a lower portion of a distillation column in the form of 1,1-dimethoxyethane. In order to produce higher purity acetic acid, distillation processes are required that have reduced mass compositions of acetals in the lower stream withdrawn from a distillation column, e.g., less than or equal to 0.03 wt. % acetal (1,1-dimethoxyethane), less than or equal to 0.025 wt. % acetal, less than or equal to 0.02 wt. % acetal, or less than or equal to 0.01 wt. % acetal. In terms of ranges, the acetal (1,1-dimethoxyethane) mass composition in the lower stream may be from 0.0001 to 0.03 wt. %, e.g., from 0.0001 to 0.025 wt. % or from 0.0001 to 0.02 wt. %.

The present invention provides processes for reducing acetal (1,1-dimethoxyethane) mass compositions during acetic acid purification. Without being bound by theory, the present invention may enhance the equilibrium reaction to reduce the acetalization towards formation of acetal and less acetaldehyde may be concentrated in the lower portion of a distillation column. In one embodiment, the processes described herein may inhibit or reduce the acetal mass composition in a distillation step that satisfies at least one of the following operating conditions: (i) temperature in a lower portion of the distillation column is not less than 40° C.; (ii) a water mass composition in the lower stream is not less than 0.3 wt. %; or (iii) acetic acid mass composition in the lower stream on weight percentage basis is greater than the acetic acid mass composition in the first mixture. In some embodiments, a distillation step that satisfies at least one of the above mentioned operating conditions reduces the acetal mass composition by at least 10% relative to distillation step not operating with the above conditions, e.g., by at least 15%, by at least 20%, by at least 25%, by at least 30%, or by at least 35%.

By operating a distillation column that satisfies at least one of operating conditions (i)-(iii), acetaldehyde can be efficiently separated to a top fraction of the distillation column and less 1,1-dimethoxyethane is concentrated in the lower stream of the distillation column. Based on these findings, the inventors have found that controlling the operating conditions in the distillation column can reduce or inhibit formation of 1,1-dimethoxyethane, thereby allowing more acetaldehyde to distribute to the top fraction of the distillation column. Additionally, the operating conditions in the distillation column inhibit or reduce 1,1-dimethoxyethane formation in the lower stream of a distillation column, and less acetaldehyde is recycled to the carbonylation reactor leading to decreased impurities in the product stream and a high-quality acetic acid product. By having lower amounts of 1,1-dimethoxyethane, the acetaldehyde can be efficiently separated in the top fraction of the distillation column.

Additionally, it was also found that the pressure in the distillation column can also impact the distillation of acetaldehyde in the mixture to the column. The use of a single high pressure distillation column that operated at higher distillation temperatures than an atmospheric distillation column can provide efficient acetaldehyde separation in combination with the aforementioned operating conditions.

For operating condition (i), the temperature in a lower portion of the distillation column is not less than 40° C., e.g., not less than 42° C., not less than 44° C., not less than 46° C., not less than 48° C., not less than 50° C., not less than 60° C., not less than 70° C., not less than 80° C., not less than 90° C., not less than 100° C., not less than 110° C., or not less than 115° C. In terms of ranges, the temperature in a lower portion of the distillation column ranges from 40° C. to 165° C., e.g., from 50° C. to 160° C., from 60° C. to 155° C., from 70° C. to 150° C., from 80° C. to 140° C., from 90° C. to 135° C., from 100° C. to 140° C., from 110° C. to 135° C., or from 115° C. to 130° C. In terms of upper limits, the temperature in a lower portion of the distillation column is less than 165° C., e.g., less than 160° C., less than 155° C., less than 150° C., less than 145° C., less than 140° C., less than 130° C., less than 125° C., or less than 120° C. The ranges disclosed in this application include the endpoints, subranges and individual values.

For operating condition (ii), a water mass composition in a lower portion of the distillation column is not less than 0.3 wt. %, e.g., not less than 0.4 wt. %, not less than 0.5 wt. %, not less than 0.6 wt. %, not less than 0.8 wt. %, not less than 1 wt. %, not less than 1.5 wt. %, or not less than 2 wt. %. In terms of ranges, the water mass composition in a lower portion of the distillation column ranges from 0.3 wt. % to 20 wt. %, e.g., from 0.5 wt. % to 18 wt. %, from 0.8 wt. % to 16 wt. %, from 1 wt. % to 15 wt. %, from 1.5 wt. % to 14 wt. %, from 2 wt. % to 12 wt. %, from 3 wt. % to 10 wt. %, from 4 wt. % to 9 wt. %, or from 5 wt. % to 9 wt. %. The water mass composition in the lower portion of the distillation column is less than 20 wt. %, e.g., less than 18 wt. %, less than 15 wt. %, less than 10 wt. %, or less than 5 wt. %.

For operating condition (iii), the acetic acid mass composition in the lower stream on weight percentage basis is greater than the acetic acid mass composition in the first mixture. The acetic acid in the first mixture may be transferred to the lower steam predominantly than the upper stream. In some embodiments, acetic acid in lower stream is not more than 3 wt. %, e.g., not more than 2.8 wt. %, not more than 2.5 wt. %, not more than 2.2 wt. %, not more than 2 wt. %, or not more than 1.8 wt. %. To achieve these acetic acid mass composition, more than 50% of the acetic acid in the first mixture is transferred to the lower stream, e.g., more than 60%, more than 70%, more than 80% or more than 90%. The lower stream may have a ratio ($H_2O$/HOAc) of water relative to acetic acid lower than the first mixture. In one embodiment, the $H_2O$/HOAc ratio in the lower stream is from 1:10 to 1:100, e.g., from 1:15 to 1:90 or from 1:20 to 1:75. The upper stream may have a ratio ($H_2O$/HOAc) of water relative to acetic acid higher than the first mixture.

Examples of a distillation step that satisfies the operating conditions (i)-(iii) may include any distillation column in an acetaldehyde separation and removal system (e.g., an acet-aldehyde removal column). The present invention is not limited to those described above and may include, for example, a low-boiling point component removal column, a dehydration column, or a high-boiling point removal column. In this case, a first mixture (e.g., a homogenous liquid, an aqueous phase, an organic phase, etc.) to the distillation column comprises at least methanol, water, $C_1$-$C_{12}$ alkyl iodides, and a PRC (e.g., acetaldehyde). In some embodiments, the first mixture comprises a PRC (e.g., acetaldehyde) from about 0.001 wt. % to 10 wt. %, a methyl iodide mass composition of 10 wt. % to 85 wt. %, a methyl acetate mass composition from 0 wt. % to 30 wt. %, an acetic acid mass composition from 0 wt. % to 12 wt. %, a water mass composition from 1 wt. % to 95 wt. %, a dimethyl ether mass composition from 0 wt. % and 1 wt. %, and a methanol mass composition from 0.0001 wt. % to 2 wt. %. In some embodiments, the first mixture (e.g., the feed) to the distil-lation column has a methanol mass composition greater than the dimethyl ether mass composition.

In some embodiments, the pressure in the distillation column can influence the acetal equilibrium reaction. For example, applying a pressure control to the distillation column to purge gas, e.g., carbon dioxide, to control the partial pressure of specific constituents in the distillation column can affect acetal formation. In some embodiments, inside of the distillation column, the column top pressure is set to, for example, 80 to 160 kPa (gauge pressure), and the column bottom pressure is higher than the column top pressure and is set to, for example, 85 to 180 kPa (gauge pressure). In some embodiments, the column top tempera-ture is, for example, a temperature of lower than the boiling point of acetic acid at the set column top pressure and is set to 90 to 130° C., and the column bottom temperature is, for example, a temperature of not less than the boiling point of acetic acid at the set column bottom pressure and is set to 120 to 165° C. (e.g., 125 to 160° C.).

In one embodiment, acetals formed in the carbonylation process may be decreased by separating the first mixture, or a derivative stream thereof, in a distillation column that is operated at an increased pressure. In separating acetic acid from the crude mixture, there may be several distillation columns and the acetal mass composition may be reduced by operating at least one of the several distillation columns at an increased pressure. In some embodiments, one of the columns in the separation may be operated at a higher pressure than the other columns to further enhance acetal hydrolysis within that column.

EMBODIMENTS

According to some embodiments, the present invention provides a process for separating or removing permanganate reducing compounds (e.g., acetaldehyde) from a first mix-ture containing at least methanol, water, $C_1$-$C_{12}$ alkyl iodides (methyl iodide as well as other alkyl iodides), and a permanganate reducing compound (a PRC or PRC's includ-ing acetaldehyde). The process for producing acetic acid is capable of lowering acetaldehyde amounts in the process streams. The process for producing acetic acid according to the present invention comprises at least one distillation step that satisfies at least one of the following operating condi-tions (i) temperature in a lower portion of the distillation column is not less than 40° C.; (ii) water mass composition in the lower stream is not less than 0.3 wt. %; or (iii) acetic acid mass composition in the lower stream on weight percentage basis is greater than the acetic acid mass composition in the first mixture; wherein the methanol mass composition in the first mixture is less than or equal to 2 wt. %.

In some embodiments, the process comprises distilling a first mixture in a distillation step to form at least two streams selected from an overhead stream, a side-cut stream, and a lower stream. A distillation column satisfying at least one of operating conditions (i)-(iii) produces a mass composition zone of PRC's and at least methyl iodide and water in a top portion of the distillation column (e.g., between the over-head stream and the feed stream) to efficiently separate PRC's. At the aforementioned operating conditions, less acetaldehyde is distributed to the lower portion of the distillation column due to the reduced acetal amounts, thereby forming a concentration zone of PRC's above the lower portion of the distillation column. In the distillation column, an extractant (or an extraction solvent) which can extract PRC's preferentially to methyl iodide is added to a concentration zone (e.g., a high concentration zone) of PRC's. In some embodiments, an extraction mixture (e.g., a liquefied fraction) falling from the concentration zone is withdrawn as the side-cut stream.

In some embodiments, no extractant is added to the distillation column. For example, no additional water (other than water in the reflux to the distillation column, if reflux is utilized) may be supplied to the distillation column. The distillation of the first mixture at least one of operating conditions (i)-(iii) may allow at least a portion of water in the first mixture to rise to an upper position than the feed port, forming a second mixture containing the portion of water and the second mixture may be withdrawn as the upper stream. The lower stream may have a water amount lower than the first mixture and the lower stream may be withdrawn from a position lower than the feed port. The lower stream may have a ratio of acetal to PRC's lower than the second mixture. In this way, distillation of the first mixture may form a concentration zone of PRC's at an upper position than the feed port of the distillation column and allows at least a portion of water in the first mixture to rise (or move upward) to the concentration zone; and a stream or fluid of the concentration zone may be withdrawn as an upper stream. In this process, a mixture falling from the concentration zone may be withdrawn as a side-cut stream.

FIG. 1 shows a continuous process 10 for producing acetic acid according to some embodiments of the present invention. In this process 10, acetic acid is produced from a reaction mixture produced by carbonylation reaction of methanol with carbon monoxide in the presence of a catalyst system comprising a rhodium catalyst as a metal catalyst and a co-catalyst as well as acetic acid, methyl acetate, and a finite (or limited) amount of water. The process 10 may comprise at least a reactor 100, a flasher 200, a first distillation column 300, a first liquid-liquid separation unit 400, and a second distillation column 500. Among these steps, the present invention comprises at least a reactor 100, a flasher 200, a first distillation column 300, and a second distillation column 500.

It should be understood to those skilled in the art that various processing equipment is now shown in detail in FIG. 1, including heat exchangers, receivers, pumps, controls, valves, etc. Unless stated otherwise, the absence of such processing equipment would be understood by one skilled in the art that such processing equipment would be used as appropriate.

The reactor 100 (e.g., a reaction system or a reactor) may carry out a carbonylation reaction of methanol. The flasher 200 may separate a reaction mixture containing acetic acid into a volatile phase 202 (e.g., lower boiling point fraction) and a less-volatile phase 204 (e.g., higher boiling point fraction). The first distillation column 300 (e.g., a splitter column) may separate the volatile phase 202 into a first overhead stream 302, an acetic acid stream 304 as a side-cut stream, and a lower stream 306 (e.g., higher boiling point fraction). The first liquid-liquid separation unit 400 may condense the first overhead stream 302 to form two phases. The second distillation column 500 (e.g., a second distillation column) may separate a first (feed) mixture comprising any one of the first overhead stream 302 (directly from the first distillation column), an aqueous phase 402 or an organic phase 404 formed in the first liquid-liquid separation unit 400 (e.g., decanter), or combinations thereof, into a second overhead stream 502, a sidecut stream 504, and a lower stream 506.

Reaction Step (Reactor)

FIG. 1 shows a continuous process 10 for producing acetic acid. As shown, methanol-containing feed stream 102 and carbon monoxide-containing feed stream 104 are directed to carbonylation reactor 100, in which the carbonylation reaction occurs to produce acetic acid. The carbonylation reaction may use a homogeneous catalyst and operates on a continuous basis (e.g., continuous process).

Methanol-containing feed stream 102 may comprise at least one member selected from the group consisting of methanol, dimethyl ether, and methyl acetate. Methanol-containing feed stream 102 may be derived in part from a fresh feed or may be recycled from the process 10. At least some of the methanol and/or reactive derivative thereof will be converted to methyl acetate in the liquid medium by esterification with acetic acid. The unreacted methanol amounts in reactor 100 is low due to high conversion and may be less than or equal to 1 wt. % based on the whole liquid phase in the reactor 100, e.g., less than or equal to 0.8 wt. %, less than 0.5 wt. %, or less than 0.3 wt. %.

Carbon monoxide-containing feed stream 104 may comprise primarily carbon monoxide of greater than or equal to 95 wt. %, e.g., greater than or equal to 97 wt. % or greater than or equal to 99 v %. In some embodiments, minor impurities such as hydrogen, carbon dioxide, oxygen, and/or nitrogen may be present in amount of less than 5 wt. %, e.g., less than 3 wt. % or less than 1 wt. %. These minor impurities may also be generated by various side reactions under operating conditions.

In some embodiments, the methanol-containing feed stream 102 and/or the carbon monoxide-containing stream 104 may include impurities. For example, the methanol-containing feed stream 102 may include metal ions that affect the purity of the methanol-containing feed stream 102. In certain embodiments, the methanol-containing feed stream 102 may have a very low metal ion content, in particular, the methanol-containing feed stream 102 may have a very low zinc ion content. The metal ion amounts in the methanol-containing feed stream 102 or the carbon monoxide-containing feed stream 104 may be less than 10 ppm by weight. For example, the metal ion mass composition may be less than 1 ppm, less than 0.5 ppm, or less than 0.1 ppm, by weight. To reduce impurities, there may be a pre-treatment step using a cation-exchange-resin column prior to being introduced into reactor 100.

In some embodiments, the feed streams or process streams directed to the reactor 100 may be pre-treated before being introduced into the reactor. For example, impurities (e.g., aminic and/or metallic) can be removed from the feed or process streams directed to the reaction step in a pre-treatment step. For purposes of the process described herein commercially available methanol may be used. Methanol-containing feed stream may be derived in part from a fresh feed from a reservoir tank (not shown), a recycled feed from the system, or a combination of fresh and recycles feeds. At least some of the methanol and/or reactive derivatives thereof will be converted to, and hence present as, methyl acetate in the liquid medium by esterification reaction with acetic acid.

The carbonylation catalyst system usually contains a metal catalyst (such as a cobalt catalyst, a rhodium catalyst, or an iridium catalyst), a catalyst stabilizer or reaction accelerator, and a co-catalyst. The metal catalysts may be used alone or in combination. The metal catalyst may preferably include a rhodium catalyst and an iridium catalyst (in particular, a rhodium catalyst).

The metal catalyst may be used in the form of a simple metal, a metal oxide (including a complex metal oxide), a metal hydroxide, a metal iodide, a metal carboxylate (e.g., an acetate), a metal salt of an inorganic acid (e.g., a sulfate, a nitrate, and a phosphate), or a metal complex. In some embodiments, the metal catalyst is in a form (e.g., a complex form) dissolvable in a liquid phase. The rhodium catalyst may include, for example, a rhodium iodide complex {e.g., $RhI_3$, $RhI_2(CO)_4]^-$, and $[Rh(CO)_2I_2]^-$} and a rhodium carbonyl complex.

In some embodiments, the reaction mixture may include a catalyst stabilizer or a reaction accelerator. The catalyst stabilizer or reaction accelerator may include a metal iodide capable of producing an iodide ion in the reaction mixture, for example, an alkali metal iodide (e.g., lithium iodide, sodium iodide, and potassium iodide). In some embodiments, the stabilizer may include lithium iodide. These co-catalysts or accelerators may be used alone or in combination. In some embodiments, the catalyst stabilizer or reaction accelerator in the whole liquid phase in the reactor has a mass composition of about 1 to 25 wt. %, e.g., about 2 to 22 wt. %, about 3 to 20 wt. %, about 4 to 18 wt. %, about 5 to 16 wt. %, or about 8 to 15 wt. %.

The reaction mixture may include acetic acid, methyl acetate formed by a reaction of acetic acid and raw material methanol, and water. Moreover, the reaction mixture usually contains unreacted raw material methanol. In some embodiments, the mass composition of methyl acetate in the reaction mixture is maintained to be from 0.5 to 30 wt. %, e.g., from 0.3 to 20 wt. %, from 0.6 to 9 wt. %, or from 0.6 to 4.1 wt. %. The mass composition of methyl acetate in the reaction mixture may be about 0.1 to 30 wt. %, e.g., from about 0.3 to 20 wt. %, from about 0.5 to 10 wt. %, or from about 0.5 to 6 wt. %.

In some embodiments, the reaction mixture includes a metal catalyst, e.g., cobalt, rhodium, iridium, or combinations thereof, in an amount from 200 to 3000 ppm (weight ppm), e.g., from 800 to 3000 wppm, from 850 to 200 wppm, or from 900 to 1500 wppm. In some embodiments, the mass composition of methyl iodide in the reaction mixture is maintained to be from 1 to 25 wt. %, e.g., from 2 to 22 wt. %, from 4 to 20 wt. %, from 5 to 15 wt. %, or from 4 to 13.9 wt. %. In some embodiments, the mass composition of iodide salt, e.g., lithium iodide, in the reaction mixture is maintained to be from 1 to 25 wt. %, e.g., from 2 to 20 wt. %, from 3 to 18 wt. %, from 4 to 15 wt. %, from 5 to 14 wt. %. The iodide salt may be formed in situ, for example, by adding lithium acetate, lithium carbonate, lithium hydroxide or other lithium salts of anions compatible with the reaction mixture. In some embodiments, the process may maintain a mass composition of lithium acetate in the reaction mixture from 0.3 to 0.7 wt. %, e.g., from 0.3 to 0.6 wt. %.

There are low amounts of water in the reaction mixture. In some embodiments, the water mass composition in the reaction mixture may be from about 0.1 to 15 wt. %, e.g., from about 0.5 to 10 wt. %, from about 0.8 to 5 wt. %, from about 1 to 3 wt. %, from about 1 to 10 wt. %, or from about 2 to 5 wt. %. In some embodiments, the reaction is conducted under low water conditions and the reaction mixture includes water in an amount from 0.1 to 4.1 wt. %, e.g., from 0.1 to 3.1 wt. % or from 0.5 to 2.8 wt. %. In some embodiments, the mass composition of acetic acid in the reaction mixture is generally more than 30 wt. %, e.g., more than 40 wt. % or more than 50 wt. %. The acetic acid in the reaction mixture functions as solvent and includes acetic acid previously charged into the reactor upon start-up.

In the acetic acid production process, formic acid is an undesirable impurity produced as a byproduct in the carbonylation reactor and deteriorates the quality of the acetic acid product. To reduce or limit formation of formic acid, the water mass composition may be controlled as well as the temperature of the reactor. Any formic acid produced by the reactor may be decomposed throughout the process rather than separated by distillation. In one embodiment, formic acid may be controlled by the water content in the reactor and/or temperature of reactor resulting in a formic acid content in the acetic acid product that is less than 200 wppm, e.g., less than 180 wppm, less than 160 wppm, less than 140 wppm, less than 120 wppm, or less than 100 wppm.

The components of the reaction mixture are maintained within defined limits to ensure sufficient production of acetic acid and utilization of reactants, while limiting the production of byproducts. In a continuous process, the amounts of components are maintained within the ranges provided and fluctuations within these ranges are anticipated. One of ordinary skill would readily understand how to control the process to maintain the amounts of components in the reaction mixture.

In some embodiments, the temperature of the carbonylation reaction may be, for example, 150° C. to 250° C., e.g., from 175° C. to 230° C. or from 185° C. to 205° C.

The reaction pressure (total reactor pressure), including partial pressures of by-products, may be, for example, about 1.5 to 4 MPa (absolute pressure) or about 2 to 3.5 MPa (absolute pressure). In some embodiments, the carbon monoxide partial pressure (absolute pressure) in the reactor can be from 0.2 MPa to 3 MPa, e.g., from 0.3 MPa to 1.8 MPa, 0.4 MPa to 1.5 MPa, or from 0.6 MPa to 1.2 MPa. The lower limit of the carbon monoxide partial pressure (absolute pressure) is not less than 0.2 MPa, e.g., not less than 0.3 MPa, not less than 0.4 MPa, or not less than 0.6 MPa.

In some embodiments, the carbon dioxide partial pressure (absolute pressure) in the reactor can be less than or equal to 110 kPa, e.g., less than or equal to 105 kPa, or less than or equal to 70 kPa. In some embodiments, the carbon dioxide partial pressure (absolute pressure) in the reactor can range from 0 kPa to 110 kPa, e.g., 0 kPa to 105 kPa, 0 kPa to 100 kPa, 0 kPa to 90 kPa, 0 kPa to 80 kPa, or 0 kPa to 70 kPa. Although the lower limit of the carbon dioxide partial pressure (absolute pressure) can be 0 kPa, the carbon dioxide partial pressure (absolute pressure) may be more than 0.1 kPa, e.g., more than 0.5 kPa, more than 1 kPa, more than 2 kPa, more than 4 kPa, or more than 5 kPa.

Carbon dioxide, while not participating in the carbonylation reaction, may be present in small amounts in the carbon monoxide-containing feed stream 104 or produced by a gas shift reaction. Carbon dioxide, along with other gases, may be removed through a vent stream, which results in a corresponding loss of valuable carbon monoxide. In carrying out the production of acetic acid, the carbon monoxide mass compositions in the reaction mixture may be at levels of less than or equal to 5 kmol/hr in the vent stream, e.g., less than or equal to 4.5 kmol/hr or less than or equal to 4.1 kmol/hr.

Although hydrogen may increase the catalyst activity, the presence of hydrogen may also yield byproducts. To carry out the production of acetic acid, hydrogen may be fed to the reactor. Hydrogen may be fed to the reactor by recycling gaseous component(s) (including hydrogen, carbon monoxide, or other gases) exhausted in the process, if necessary after purifying and/or separating the gaseous component(s) in the succeeding step(s). In some embodiments, the hydrogen partial pressure (absolute pressure) in the reactor can be less than 500 kPa, e.g., e.g., less than 180 kPa, less than 150 kPa, less than 135 kPa, less than 125 kPa, less than 120 kPa, or less than 105 kPa. In some embodiments, the hydrogen partial pressure (absolute pressure) in the reactor can range from 0 kPa to 500 kPa, e.g., 5 kPa to 180 kPa, 5 kPa to 150 kPa, 5 kPa to 135 kPa, 5 kPa to 120 kPa, or 5 kPa to 105 kPa. Although the lower limit of the hydrogen partial pressure (absolute pressure) can be 0 kPa, the hydrogen partial pressure (absolute pressure) may be more than 1 kPa, e.g., more than 2 kPa, more than 4 kPa, or more than 5 kPa.

In the reactor, the carbonylation reaction of methanol proceeds with forming an equilibrium between a liquid-phase reaction system and a gaseous-phase system. The liquid-phase reaction system contains the reactant(s) and the metal catalyst component, and the gaseous-phase system comprises carbon monoxide, reaction products (hydrogen, methane, and carbon dioxide), and vaporized lower boiling point components (e.g., methyl iodide, acetic acid, and methyl acetate). The vapor components (vent gas) may be withdrawn from the top (or head) of the reactor, or may be subjected to an absorption treatment to recover condensable liquids, carbon monoxide and/or hydrogen which may be then recycled to the reactor.

In some embodiments, the internal pressure of the reactor 100 may be controlled by withdrawing or venting a gaseous stream 112. The gaseous stream 112 may be further processed in an absorption system 110, such as a scrubber system or a pressure swing absorption tower. In some embodiments, the gaseous stream 12 is condensed and the gaseous portion (noncondensable fraction) may be fed to the absorption system 110. In some embodiments, the gaseous portion owing to its relatively high carbon monoxide content is useful to stabilize the catalyst against precipitation. Absorption system 110 is capable of collecting and/or recovering useful components, in particular organic components as well as methyl iodide. A chilled solvent is fed via line 116 at the top of absorption unit 100 to recover such components in the residue 118, which may be returned to the reactor 100. The chilled solvent may comprise acetic acid, methanol, methyl acetate, water, or mixtures thereof, and is chilled to a temperature of less than or equal to 20° C., less than or equal to 18° C. or less than or equal to 10° C. Any remaining gaseous not collected in the residue 118 may leave the absorption system 110 near the top via line 114. Although one absorber is shown for the absorption system 110, the absorption system may comprise multiple absorption towers as well as solvent stripping columns. Further, other vent streams obtained throughout the process may be collected and passed through the absorption system 110.

One absorption system involves multiple absorbing steps, e.g., with differing absorption solvents and/or differing pressures. Such systems are described in U.S. Pat. No. 8,318, 977, which is incorporated herein by reference in its entirety.

The reaction mixture (reaction liquid) may include acetic acid, methyl iodide as a co-catalyst, methyl acetate as a reaction product of acetic acid and methanol, water, and acetaldehyde as a by-product. The reaction mixture may include such as a metal catalyst component (e.g., a rhodium catalyst), lithium iodide as a catalyst stabilizer and/or methyl iodide.

In addition to the acetic acid product, various byproducts and/or impurities may also be generated in the reaction mixture. Further, by-products derived from acetaldehyde (acetaldehyde derivatives) are also produced. The acetaldehyde derivatives may include, for example, other aldehydes such as butyraldehyde, crotonaldehyde, 2-ethylcrotonaldehyde, and 2-ethylbutyraldehyde; a ketone such as acetone or methyl ethyl ketone; an aldol condensation product thereof; and a $C_{2-12}$ alkyl iodide such as ethyl iodide, propyl iodide, butyl iodide, pentyl iodide, or hexyl iodide. The by-products may also include a 3-hydroxyalkanal (e.g., 3-hydroxybutanal); formic acid or the $C_{3-12}$ alkanecarboxylic acid (such as propionic acid, butanoic acid, hexanoic acid, heptanoic acid, or octanoic acid); a $C_{3-12}$ alkyl alcohol such as butyl alcohol or 2-ethylbutyl alcohol; an ester of methanol or the above alkyl alcohol with acetic acid or the above carboxylic acid; an ether of methanol and/or the above alkyl alcohol (a dialkyl ether such as dimethyl ether); and methane and a hydrocarbon with two or more carbon atoms (e.g., a $C_{2-12}$ alkane). Acetaldehyde and the by-products derived from acetaldehyde (for example, other aldehydes, the ketone, and the aldol condensation product) belong to permanganate reducing compounds (PRC's). Thus, it is preferred to separate and remove acetaldehyde, which is a main by-product, from the reaction mixture and to recover useful components (e.g., methyl iodide) from the process stream(s).

According to the present disclosure, acetaldehyde is efficiently separable and removable to decrease the amount of acetaldehyde in the reactor even in a continuous reaction. With the decrease in acetaldehyde amount or the elimination of acetaldehyde, production of by-products derived from acetaldehyde is significantly prevented. In particular, due to the higher content of acetaldehyde that is separated into the column top fraction (since less is trapped in the acetal), less acetaldehyde is in the lower stream that is recycled to the reactor. For example, the reactor may have a PRC (representatively, acetaldehyde) mass composition of, for example, less than 1800 wppm, e.g., less than 1600 wppm, less than 1000 wppm, or less than 800 ppm. In some embodiments, reactor may have a PRC (representatively, acetaldehyde) mass composition from 0 to 1800 wppm, e.g., 100 to 1600 wppm, 150 to 1000 wppm, or from 200 to 800 wppm.

The space time yield of acetic acid in the reaction system may be, for example, about 5 mol/L·h to 50 mol/L·h, preferably about 8 mol/L·h to 40 mol/L·h, and more preferably about 10 mol/L·h to 30 mol/L·h.

The reaction system is an exothermic reaction system that accompanies heat generation, and the reaction temperature may be controlled (or regulated) by recycling of the condensate which has been cooled or from which heat has been removed, installation of a heat-removable (or heat-removing) unit or a cooling unit (e.g., a jacket). In order to remove part of the reaction heat, a vapor (vent gas) from the reactor may be cooled in a condenser, a heat exchanger, or other means to separate the vapor into liquid components and gaseous components, and the liquid components and/or the gaseous components may be recycled to the reactor.

In some embodiments, pump-around reactors or extended reactors can be used in the carbonylation reaction step to recover heat of the reaction. For example, a pump around reactor can be positioned in a side stream from the carbonylation reactor and a portion of the reaction solution from the carbonylation reactor is fed to the pump around reactor. Carbon monoxide and a reactant selected from the group consisting of methanol, methyl acetate, methyl formate, dimethyl ether and/or mixtures can be fed to the pump around reactor. In one embodiment, the pump around reactor contains only the catalyst in the reaction solution, i.e., no additional catalyst is introduced to the pump around reactor. The pump around reactor may extend the carbonylation reaction to produce additional heat of reaction that may be recovered.

The carbonylation reaction is exothermic and temperature of the reactor may be regulated by a variety of methods. For purposes of the present disclosure, any suitable cooling may be used to regulate the temperature of the reactor. U.S. Pat. No. 5,374,774 describes a cooling unit in the recycle line for the reactor. A pump around loop may be used to generate additional heat for the production of steam while regulating the temperature of the carbonylation reactor, which is further described in U.S. Pat. No. 8,530,696. In some embodiments, the temperature of the reactor may be controlled by condensing a portion of the flash overhead that is returned to the reactor, which is further described in U.S. Pat. No. 8,957, 248.

The material of the carbonylation reactor 100 and its internals is not particularly limited and may be a metal, a ceramic, a glass, or combinations thereof. For example, the material may include zirconium-based materials and alloys that tend to have high corrosion resistance, but may also include iron-based alloys (stainless steel), nickel-based alloys (HASTELLOY™ or INCONEL™), titanium-based materials and alloys, or aluminum-based materials or alloys.

In some embodiments, the reactor 100 is self-agitating (capable of agitation), for example, a mechanically stirred vessel, a vessel with educted or pump-around mixing, or bubble-column type vessel, with or without an agitator, within which the reacting liquid or slurry contents are maintained, preferably automatically, at a predetermined level, which remains substantially constant during normal operation.

Flash Evaporation Step

In steady state operations, the reaction mixture is continuously drawn off from the carbonylation reactor 100 via line 120 at a rate sufficient to maintain a constant level therein and is provided to flasher 200. To obtain the acetic acid product, the withdrawn reaction mixture via line 120 is fed to the subsequent downstream flasher 200 (e.g., flash evaporator, flash vessel, or flash distillation). In some embodiments, a converter reactor (not shown) or a pipe reactor (not shown) can be employed in the flow path between the reactor and evaporator. A pipe reactor is described in U.S. Pat. No. 5,672,744 and is used to react the dissolved carbon monoxide in the reaction mixture. Chinese Patent No. CN1043525C describes a converter reactor to allow the reaction to proceed to a greater extent prior to subsequent flashing. The converter reactor produces a vent stream comprising gaseous components which are typically scrubbed with a compatible solvent to recover components such as methyl iodide and methyl acetate. As described herein, the gaseous stream from the reactor 10 and converter can be combined or scrubbed separately and are typically scrubbed with either acetic acid, methanol or mixtures of acetic acid and methanol, to prevent loss of low boiling components such as methyl iodide from the process.

The flasher 200 separates the reaction mixture, referred to herein as flashing or evaporating, into a volatile phase (vapor acetic product) 202 and a less-volatile phase (residual liquid catalyst stream) 204. The volatile phase 202 may include acetic acid, methyl iodide, acetaldehyde, methyl acetate, water, or other compounds, and the less-volatile phase 204 may include acetic acid, metal (cobalt, rhodium, and/or iridium) catalyst and co-catalyst compounds (including lithium iodide). At least a first portion of the volatile phase is fed to a first distillation column 300, and the less-volatile phase 204 is recycled to the reactor 100 of the reaction step via a recycle line. Although not shown in FIG. 1, a portion of the less-volatile phase 204 may be condensed and a condensate may be recycled to the reactor 100.

The respective flow rates of volatile phase 202 and less-volatile phase 204 may vary. In some embodiments, 15% to 55% of the flow (e.g., the flow of the reaction mixture via line 120) into flasher 200 is removed as volatile phase 202 and 45% to 85% of the flow is removed as the less-volatile phase 204. The ratio between the volatile phase 202 and the less-volatile phase 204 separated in the flasher 200 may be from 10:90 to 60:40 in terms of a mass ratio, e.g., 25:75 to 45:55 or 30:70 to 40:60. In some embodiments, the evaporation rate of the reaction mixture in the flasher 200 is from 10 to 60% by mass, e.g., 26 to 45% by mass, 27 to 42% by mass, or 30 to 40% by mass.

In some embodiments, less-volatile phase 204 comprises acetic acid, the metal catalyst, corrosion metals, as well as other various compounds. In one embodiment, less-volatile phase 204 comprises acetic acid in an amount from 60 to 90 wt. %, metal catalyst in an amount from 0.01 to 0.5 wt. %, corrosion metals (e.g., nickel, iron and chromium) in a total amount from 10 to 2500 wppm, lithium iodide in an amount from 5 to 20 wt. %, methyl iodide in an amount from 0.5 to 5 wt. %, methyl acetate in an amount from 0.1 to 5 wt. %, water in an amount from 0.1 to 8 wt. %, acetaldehyde in an amount of less than or equal to 1 wt. % (e.g., from 0.0001 to 1 wt. % acetaldehyde), and hydrogen iodide in an amount of less than or equal to 0.5 wt. % (e.g., from 0.0001 to 0.5 wt. % hydrogen iodide).

In one embodiment, the volatile phase 202 comprises acetic acid, methyl iodide, methyl acetate, water, acetaldehyde, and hydrogen iodide. In one embodiment, volatile phase 202 comprises acetic acid in an amount from 45 to 75 wt. %, methyl iodide in an amount from 20 to 50 wt. %, methyl acetate in an amount of less than or equal to 9 wt. %, water in an amount of less than or equal to 15 wt. %, and PRC's in an amount less than or equal to 5 wt. %, based on the total weight of the volatile phase. In another embodiment, volatile phase 202 comprises acetic acid in an amount from 45 to 75 wt. %, methyl iodide in an amount from 24 to less than or equal to 36 wt. %, methyl acetate in an amount of less than or equal to 9 wt. %, water in an amount of less than or equal to 15 wt. %, and PRC's in an amount less than or equal to 2 wt. %, based on the total weight of the volatile phase. In some embodiments, the volatile phase 202 comprises acetic acid in an amount from 55 to 75 wt. %, methyl iodide in an amount from 24 to 35 wt. %, methyl acetate in an amount from 0.5 to 8 wt. %, water in an amount from 0.5 to 14 wt. %, and PRC's in an amount less than or equal to 1 wt. %. In some embodiments, the volatile phase 202 comprises acetic acid in an amount from 60 to 70 wt. %, methyl iodide in an amount from 25 to 35 wt. %, methyl acetate in an amount from 0.5 to 6.5 wt. %, water in an amount from 1 to 8 wt. %, and PRC's in an amount less than or equal to 0.5 wt. %.

The acetaldehyde mass composition in the volatile phase 202 may be in an amount from 0.005 to 1 wt. %, based on the total weight of the volatile phase 202, e.g., from 0.01 to 0.8 wt. %, or from 0.01 to 0.7 wt. %. In some embodiments, the acetaldehyde may be present in amounts less than or equal to 0.01 wt. %. Volatile phase 202 may comprise hydrogen iodide in an amount less than or equal to 1 wt. %, based on the total weight of the volatile phase 202, e.g., less than or equal to 0.5 wt. %, or less than or equal to 0.1 wt. %. Volatile phase 202 is preferably substantially free of, i.e., contains less than or equal to 0.0001 wt. %, propionic acid, based on the total weight of the volatile phase.

In addition to acetic acid, volatile phase 202 also comprises methyl iodide, methyl acetate, water, and PRC's, e.g., acetaldehyde and crotonaldehyde. Dissolved gases exiting reactor 100 and entering flasher 200 comprise a portion of the carbon monoxide and may also contain gaseous by-products such as methane, hydrogen, and carbon dioxide. Such dissolved gases exit flasher 200 as part of the volatile phase 202. In one embodiment, carbon monoxide in gaseous purge stream may be fed to the base of flasher 200 to enhance rhodium stability.

Although not shown in FIG. 1, a portion of the volatile phase 202 may be cooled and condensed in a condenser. The resulting condensate may be held in a hold tank for recycling the condensate to the reactor 100. The cooled product (condensate and/or noncondensable component) in the condenser may be fed to a liquid-liquid separation step and may be held in a decanter together with an overhead from the first distillation step (splitter column), and a mixture of the cooled product and the overhead maybe separated into two phases in a liquid-liquid separation unit (e.g., decanter).

In some embodiments, a portion of the volatile phase 202 may be fed, without condensation, to the distillation step directly or indirectly, or may be cooled and condensed in one or a plurality of condensers to form two phases (an aqueous phase or an organic phase) for subjecting the aqueous phase or the organic phase (at least the aqueous phase) to the distillation step directly or indirectly via the liquid-liquid separation step. For example, a portion of the volatile phase 202 may optionally be condensed as described above (and optionally be liquid-liquid separated) and mix with the condensate obtained in the liquid-liquid separation step, and the mixture may be subjected to the distillation step. If necessary, the catalyst component (metal catalyst component) and the catalyst stabilizer or the reaction accelerator may be separated from the less-volatile phase 204 by one or a plurality of steps and may be recycled to the reactor 100.

The flash evaporation may include a thermostatic flash in which the reaction mixture is heated and depressurized, an adiabatic flash in which the reaction mixture is depressurized without heating, or a combination of these flash conditions. By such a flash evaporation, the reaction mixture may be separated into the vapor phase and the liquid phase. For example, the flash distillation may be carried out at a temperature of the reaction mixture of 80 to 250° C., a pressure (absolute pressure) of the reaction mixture of 10 to 1000 kPa (e.g., 100 to 1000 kPa), preferably 100 to 500 kPa, and more preferably 100 to 300 kPa. The flash evaporation may, for example, be carried out at a temperature of 80 to 250° C., e.g., 90 to 200° C., 100 to 180° C., 110 to 170° C., and 120 to 160° C. The pressure (gauge pressure) may be 0.01 to 1 MPa, e.g., 0.03 to 1 MPa, 0.05 to 0.5 MPa, 0.08 to 0.3 MPa, or 0.1 to 0.2 MPa. The less-volatile phase or the catalyst liquid mixture may have a temperature of, for example, 80 to 200° C., e.g., 90 to 180° C., 100 to 170° C., or more preferably 130 to 160° C.

Flasher 200 may be a vertical evaporator having a torispherical, ellipsoidal, or hemispherical head. To allow maintenance or access, flasher 200 may have one or more manways. Reaction mixture 120 may be tangentially fed through one or more feed ports as shown in U.S. Pat. No. 6,599,348 into flash vessel 200 in an upper portion. To direct the liquid portion downwards, a splash plate may be used in each of the feed ports. The nozzle for reaction mixture 120 may be in the upper portion of flasher 200, e.g., above the liquid level within the flasher 200. There may be one or more nozzles (not shown) that introduce the reaction mixture tangentially to further disengage the vapor portion. In some embodiments, flasher 200 may have an upper portion with a larger cylinder diameter than the lower portion. Flasher 200 should have large volume to allow the reaction mixture 120 that is fed thereto to be maintained in the flasher 200 to vaporize the desired carbonylation products into the volatile phase 202, and prior to recycling the less volatile phase 204. In one embodiment, a residence time in the flasher 200 of about one minute or more is desirable, and in some embodiments, a residence time of at least about two minutes or more may be used.

To maintain or enhance catalyst stability and reduce or prevent catalyst precipitation in flasher 200, a carbon monoxide-containing purge may be introduced to the lower section, e.g., below the feed nozzle, of the flasher 200 or into the less-volatile phase 204. The carbon monoxide-containing purge may comprise greater than 60 wt. % carbon monoxide, e.g., greater than 80 wt. %, or greater than 90 wt. %. The amount of carbon monoxide-containing purge may be sufficient to dissolve carbon monoxide into the liquid held up in the lower portion of the flasher 200. In one embodiment, the carbon monoxide-containing purge may be feed in an amount greater than 5 $Nm^3/hr$, e.g., greater than 50 $Nm^3/hr$ or greater than 100 $Nm^3/hr$. The upper limit may be 1000 $Nm^3/hr$.

Even when CO-containing purges are used to stabilize the catalyst, there may be some insoluble forms that precipitate onto the interior surface. Owing to its relative expense, insoluble forms of rhodium that collect on the interior surface may be recovered for reuse.

In operating the process continuously, there may be some catalyst loss, thus necessitating the use of makeup catalyst. Although makeup catalyst may be added directly to reactor 100, in one embodiment, the makeup catalyst may be added to the flasher 200 or to line for the less volatile phase 204. The makeup catalyst may be metered at a rate sufficient to maintain the continuous reaction.

In some embodiments, an optional mist eliminator may be employed near the vapor outlet to coalesce liquid droplets. An optional scrubbing section (not shown) may further be employed in the vapor outlet of the flasher to prevent and/or reduce entrainment from metallic catalysts or other metallic components into the volatile phase 202. A wash liquid may be introduced into the optional scrubbing section. In another embodiment, an in-line separator may be used in the line for the volatile phase 202 to impart a swirling motion and to allow entrained liquid to coalesce. The liquid may be drained back to flasher 20 to reduce entrainment in volatile phase 202.

In some embodiments, the less-volatile phase 204 may be treated to remove corrosive metals (e.g., nickel, iron and chromium). For example, prior to recycling the less-volatile phase 204 to the reactor 100, a slip stream may pass through a corrosion metal removal bed, e.g., an ion exchange bed, to remove any entrained corrosion metals, such as nickel, iron, chromium, and molybdenum, as described in U.S. Pat. No. 5,731,252, which is incorporated herein by reference in its entirety. Also, the corrosion metal removal bed may be used to remove nitrogen compounds, such as amines, as described in U.S. Pat. No. 8,697,908, which is incorporated herein by reference in its entirety.

First Distillation Step (First Column or Splitter Column)

As shown in FIG. 1, the volatile phase 202 is directed to a first distillation column 300 in a first distillation step, also known as a splitter column or a light ends column. To allow for separation, the first distillation column 300 may comprise a plate column, a packed column or combination thereof. In the embodiments that use a plate column, the theoretical number of plates may range from 5 to 80 plates, e.g., from 10 to 60 plates or from 15 to 50 plates. In the first distillation column 300, the volatile phase 202 (or a portion thereof) is separated into a first overhead stream 302, an acetic acid stream 304, and a lower stream 306. The first overhead stream 302 (overhead gas, lower boiling point stream or lower boiling point fraction) is withdrawn from a top or upper position (or part) of the column, the acetic acid stream 304 is withdrawn as a side-cut from a position between the upper position and lower position and mainly contains acetic acid, and the lower stream 306 (higher boiling point stream or higher boiling point fraction) is withdrawn from a bottom or lower position (or part) of the first distillation column 300. A majority of the acetic acid is removed in acetic acid stream 304 and preferably little or no acetic acid is recovered from lower stream 306. The proportion of the first overhead stream 302 may be about 20% to 60% of the whole volatile phase 202, e.g., about 35% to 50%. The proportion of the acetic acid stream 304 may be about 30% to 80%, e.g., about 40% to 70%, of the whole volatile phase 202. The proportion of the lower stream 306 may be about 0% to 10%, e.g., from about 0% to 3%, of the whole volatile phase 202.

The first overhead stream 302 contains at least both permanganate reducing compound (PRC) and methyl iodide. The PRC contains at least by-product acetaldehyde. The first overhead stream 302 usually contains methyl acetate and practically contains acetic acid, methanol, water, dimethyl ether, and/or by-products derived from acetaldehyde (e.g., an aldehyde such as crotonaldehyde or butyraldehyde; an acetaldehyde derivative such as a $C_{2\text{-}12}$ alkyl iodide or a $C_{3\text{-}12}$ alkanecarboxylic acid; and a $C_{2\text{-}12}$ alkane).

In one embodiment, first overhead stream 302 comprises water in amount greater than or equal to 5 wt. %, based on the total weight of the first overhead stream 302, e.g., greater than or equal to 10 wt. %, or greater than or equal to 25 wt. %. In some embodiments, the amount of water may be up to 80 wt. %. In terms of ranges, water mass composition in the overhead may be from 5 wt. % to 80 wt. %, e.g., from 10 wt. % to 70 wt. % or from 25 wt. % to 60 wt. %. Reducing water mass composition to less than 5 wt. % is not advantageous because this results in a large recycle of acetic acid back to the reaction system which then sets up a large recycle through the entire purification system. In addition to water, first overhead stream 302 may also comprise methyl acetate, methyl iodide, and carbonyl impurities, which are preferably concentrated in the overhead to be removed from acetic acid in acetic acid stream 304. These carbonyl impurities may also be referred to herein as PRC's.

The first overhead stream 302 from the first distillation column 300 is cooled and condensed in one or more condensers 350. The condensate 352 can be biphasically separable into an aqueous phase rich in water and an organic phase rich in methyl iodide in the first liquid-liquid separation unit (e.g., decanter) 400. In some embodiments, the first overhead stream 302 is cooled in a plurality of condensers (e.g., a plurality of condensers successively lower in cooling temperature) arranged in series to form a plurality of condensates successively lower in temperature. For example, the condensate formed in a first condenser among the plurality of condensers may have a temperature from 10° C. to 120° C., e.g., from 20° C. to 110° C., from 30° C. to 100° C., from 40° C. to 90° C., from 50° C. to 80° C., or from 60° C. to 70° C. In some embodiments, the condensate formed in a second condenser among the plurality of condensers may have a temperature from −30° C. to 60° C., e.g., from −20° C. to 50° C., from −15° C. to 45° C., from −5° C. to 40° C., from 0° C. to 30° C., or from 5° C. to 20° C.

In some embodiments, at least a portion of the condensate 352 is directly refluxed to the first distillation column 300. In some embodiments, at least a portion of the condensate 352 is directed to a first liquid-liquid separation unit 400 to form an aqueous phase 402 and an organic phase 404. Conditions are desirably maintained in the first liquid-liquid separation unit 400 such that the condensate 352 may separate to form an aqueous phase 402 and an organic phase 404. The phase separation should maintain two separate phases, without forming a third phase or emulsion between the phases.

In some embodiments, a portion of the condensate 352, the aqueous phase 402 and/or the organic phase 404 can be returned to the first distillation column 300 via reflux lines 406 or 408, respectively. Depending on the need to remove PRCs (including acetaldehyde), at least a portion of the aqueous phase 402 is fed to a second distillation column 500, and at least a portion of the organic phase 404 may be recycled to the reactor 100 via return line 416. In some embodiments, a portion of the condensate 352, the aqueous phase 402 and/or the organic phase 404 can be returned to the reactor 100 via return lines 414 or 416, respectively. Thus, in one embodiment, a portion of the aqueous phase is 402 returned to the first distillation column 300 for reflux via line 406, the residual portion of the aqueous phase 402 is fed to the second distillation column 500 via line 410, and a portion or the entire portion of the organic phase 404 is returned to the reactor 100 via line 416. In another embodiment, a portion of the aqueous phase 402 is returned to the first distillation column 300 for reflux via line 406, and a portion of the organic phase 404 is directed to the second distillation column 500 via line 412, and another portion of the organic phase 404 is returned to the reactor via line 416. In another embodiment, a portion of the aqueous phase 402 is returned to the first distillation column 300 for reflux via line 406, and a portion of the aqueous phase 402 and organic phase 404 is directed to the second distillation column 500 via lines 410 and 412, and another portion of the organic phase 404 is returned to the reactor via line 416. Any remaining aqueous phase 402 not refluxed or fed to second distillation column 500 is returned to the reactor 100 via line 414.

In some embodiments, a portion (or whole) of the aqueous phase 402 (or a process stream derived from the aqueous phase) can be fed to the second distillation column 500 or at least a portion of the organic phase 404 (or the whole organic phase) can be fed to the second distillation column 500. In some embodiments, at least a portion of the organic phase 404 (the organic phase rich in methyl iodide) is refluxed to the first distillation column 300 via line 406, and at least a portion of the aqueous phase 402 may be fed to the second distillation column 500 via line 410.

The reflux ratio (amount refluxed/amount distilled) of the condensate 352, the aqueous phase 402 and/or the organic phase 404 to the first distillation column 300 can be controlled to further separate or remove impurities. Owing to the higher water content, the aqueous phase 402 may be more suited for reflux. In refluxing aqueous phase 402, and only the aqueous phase, to the first distillation column 300, a reflux ratio of the aqueous phase may be from 0.2 to 15, e.g., from 1.5 to 15, from 1.8 to 10 or from 1.8 to 5. Although a portion of organic phase 404 may be refluxed to the first distillation column 300 via line 408, either alone or in combination the aqueous phase 402, it is more desirable to return the methyl iodide enriched organic phase to the reactor 100 via line 416. Thus, a portion of the organic phase 404 may also be refluxed via line 408 with the aqueous phase 402, and the total reflux may also be from 0.2 to 15.

In this way, the crotonaldehyde in the top portion of the first distillation column 300 can be controlled to less than 5.0 ppm by mass, e.g., less than 4.5 ppm by mass, less than 4.0 ppm by mass, less than 3.5 ppm by mass, less than 3.0 ppm by mass, less than 2.5 ppm by mass, less than 2.0 ppm by mass, less than 1.8 ppm by mass, less than 1.5 ppm by mass, less than 1.2 ppm by mass, less than 1.0 ppm by mass, or less than 0.8 ppm by mass, or less than 0.5 ppm by mass. In some embodiments, the first distillation column 300 is operated to have a minimal crotonaldehyde mass composition for higher purity acetic acid product. Crotonaldehyde causes deterioration in a potassium permanganate test value (permanganate time) of acetic acid. Furthermore, crotonaldehyde reacts with acetaldehyde to produce 2-ethyl crotonaldehyde. Although 2-ethyl crotonaldehyde also causes deterioration in the potassium permanganate test value of acetic acid, the degree of potassium permanganate test deterioration per mass of 2-ethyl crotonaldehyde is much smaller than that of crotonaldehyde.

In addition to the first liquid-liquid separation unit 400 (e.g., decanter) for temporarily holding or retaining the condensate and biphasically separating the condensate, a buffer tank for temporarily holding (or retaining) the condensate may optionally be utilized.

In some embodiments, an offgas may be vented from the liquid-liquid separation unit 400 400. In some embodiments, the average residence time of the condensed first overhead stream 302 in the first liquid-liquid separation unit 400 is greater than or equal to 1 minute, e.g., greater than or equal to 3 minutes, greater than or equal to 5 minutes, greater than or equal to 10 minutes, and/or the average residence time is less than or equal to 60 minutes, e.g., less than or equal to 45 minutes, or less than or equal to 30 minutes, or less than or equal to 25 minutes.

For example, the aqueous phase, which is primarily water, may have the following composition shown in Table 1.

TABLE 1

| Exemplary Aqueous Phase Compositions from First Column Overhead | | |
| --- | --- | --- |
| | (Wt. %) | (Wt. %) | (Wt. %) |
| Water | 40-80 | 50-75 | 60-75 |
| Methyl Acetate | 1-50 | 1-25 | 1-15 |
| Acetic Acid | 1-40 | 1-25 | 5-15 |
| Methanol | <5 | <1 | 0.01-3.5 |

TABLE 1-continued

| Exemplary Aqueous Phase Compositions from First Column Overhead | | | |
| --- | --- | --- | --- |
| | (Wt. %) | (Wt. %) | (Wt. %) |
| PRC's | <5 | <3 | <1 |
| Methyl Iodide | <10 | <5 | <3 |

For example, the organic phase, which is primarily methyl iodide, may have the following composition shown in Table 2.

TABLE 2

| Exemplary Organic Phase Compositions from First Column Overhead | | | |
| --- | --- | --- | --- |
| | (Wt. %) | (Wt. %) | (Wt. %) |
| Methyl Iodide | 60-98 | 60-95 | 80-90 |
| Methyl Acetate | 0.1-25 | 0.5-20 | 0.7-15 |
| Acetic Acid | 0.1-10 | 0.5-10 | 0.7-10 |
| Hydrogen Iodide | <1 | <0.5 | 0.001-0.5 |
| Methanol | <2 | <1 | <0.5 |
| Water | <3 | 0.05-1 | 0.01-1 |
| PRC's | <5 | <3 | 0.05-0.5 |

A portion of the organic phase 404, which is primarily methyl iodide, is returned (recycled) to the reactor 100. In some embodiments, a portion of organic phase 404 may be refluxed alone or with the aqueous phase 402 to the first distillation column 300. The specific gravity of organic phase 404 may be from 1.3 to 2, e.g., from 1.5 to 1.8, from 1.5 to 1.75 or from 1.55 to 1.7. As described in U.S. Pat. No. 6,677,480, the measured specific gravity in organic phase 404 may correlate to the methyl acetate mass composition in the reaction mixture. As specific gravity decreases, the methyl acetate mass composition in the reaction mixture increases. In some embodiments, a receiver is arranged and constructed to maintain a low interface level to prevent an excess hold up of methyl iodide. The ratio, based on weight, of the flow rate of the aqueous phase withdrawn from the receiver relative to that of the organic phase withdrawn from the receiver may be, for example, about 0.1/1 to 10/1 (e.g., about 0.3/1 to 3/1), or about 0.5/1 to 2/1 (e.g., about 0.7/1 to 1.5/1).

Off-gases may be vented from the first distillation column 300 and/or liquid-liquid separation unit 400 as needed and directed to an absorption unit.

In a continuous process, there may be variations in flow, which if left unregulated may cause disruptions and processing difficulties. To account for these variations the process may deploy a hold tank to buffer the streams between the first distillation column 300 and liquid-liquid separation unit 400, or after the receiver for either aqueous phase or organic phase. When used, the hold tank is sized to account for up to 20% variations in flow entering and leaving the receiver.

Second Distillation Step

Figure 2:
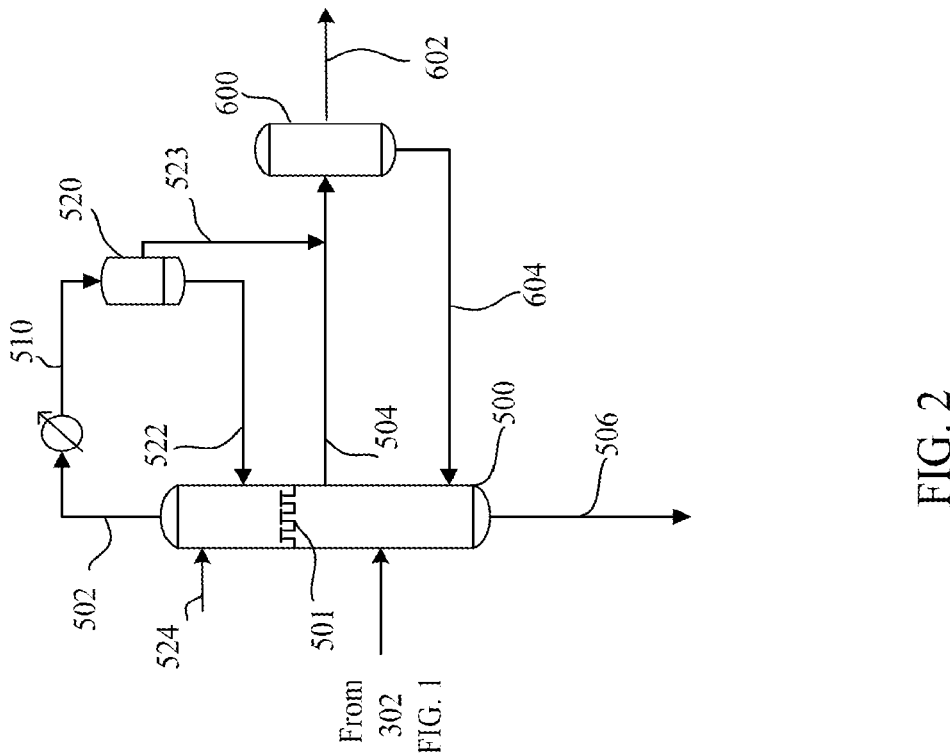
FIG. 2 illustrates a schematic flow diagram of an acetaldehyde separation column in accordance with some embodiments of the present invention.

As shown in FIG. 2, a first mixture is directed to a second distillation column 400 in a second distillation step. Although FIG. 2 shows that the first mixture to the second distillation column as the first overhead stream 302 from the first distillation column 300, the first mixture can be multiple different combinations of process streams. For example, the process streams introduced to the second distillation column 400 may include the first overhead stream 302 and phases biphasically separated therefrom (aqueous phase 402 and/or organic phase 404), the acetic acid stream 304 and phases biphasically separated therefrom, or condensates of any of the streams. The first mixture is represented as the first overhead 302, but it should be understood that the first mixture may comprise a portion of the first overhead 302 including the liquid-liquid separated aqueous phase and organic phases described above.

In one embodiment, a portion of the first overhead 302 (either the aqueous phase or organic phase, or combinations thereof) may be introduced into a second distillation column 500, where acetaldehyde is removed in an second overhead 502, and 1,1-dimethoxyethane, including 1,1-dimethoxyethane formed within the column, falls down the column 500 and into the lower stream 506. The distillation may be conducted either as batch distillation or continuous distillation. To allow for separation, the second distillation column 500 may comprise a plate column, a packed column or combination thereof. In the embodiments that use a plate column, the theoretical number of plates thereof, may range from 1 to 100 plates, e.g., from 2 to 80 plates or from 5 to 75 plates.

In the present invention, the second distillation column 500 should satisfy at least one of the following operating conditions: (i) temperature in a lower portion of the distillation column is not less than 40° C.; (ii) a water mass composition in the lower stream is not less than 0.3 wt. %; and/or (iii) acetic acid mass composition in the lower stream, based on the total weight of the lower stream, is greater than the acetic acid mass composition in the first mixture. By operating the second distillation column 500 at any one of operating conditions (i)-(iii), acetaldehyde can be efficiently separated to a upper stream (second overhead stream 502 or sidecut stream 504) of the distillation column and less 1,1-dimethoxyethane is formed and is concentrated in the lower stream of the second distillation column 500. The aforementioned operating conditions in the distillation column can reduce or inhibit formation of 1,1-dimethoxyethane, thereby allowing more acetaldehyde to distribute to the upper stream of the second distillation column 500. The withdrawn lower stream 506 from the second distillation column 500 can be (e.g., directly) recycled to the carbonylation reactor 100 and with less impurities (e.g., acetaldehyde and/or 1,1-dimethoxyethane) for a higher purity acetic acid product. A distillation step that satisfies the aforementioned conditions has a methanol mass composition in the first mixture (aqueous portion in line 410 or organic portion in line 412) to the distillation column of less than or equal to 2 wt. %, e.g., less than or equal to 1 wt. % or less than or equal to 0.5 wt. %. In some embodiments, the first mixture (which may also be referred to as the feed mixture) to the second distillation column 500 has a methanol mass composition greater than the dimethyl ether mass composition.

The inventors have found that by controlling the amount of 1,1-dimethoxyethane in the lower stream of the distillation, acetaldehyde can be efficiently separated in the second distillation column 500. Due to the lower amounts of 1,1-dimethoxyethane in the lower portion of the second distillation column 500, less acetaldehyde is concentrated in the lower stream that is withdrawn from the distillation column. As a result, acetaldehyde in the first mixture or first overhead 302 (e.g., feed mixture) to the second distillation column 500, which can be either the aqueous and/or organic phases, is efficiently separated and distributed to an upper portion of the distillation column to form a concentration of zone of PRC's (e.g., at least including acetaldehyde). The acetaldehyde in the mass composition can be preferentially separated from the concentration zone by adding an extractant (e.g., water) to the second distillation column 500. In particular, the extractant can be added to the concentration zone of PRC's to extract acetaldehyde preferentially than other components, thereby providing efficient separation of acetaldehyde in the second distillation column 500.

For operating condition (i), a temperature in a lower portion of the second distillation column 500 is 40° C. or more, e.g., 42° C. or more, 44° C. or more, 46° C. or more, 48° C. or more, 50° C. or more, 60° C. or more, 70° C. or more, 80° C. or more, 90° C. or more, 100° C. or more, 110° C. or more, or 115° C. or more. In terms of ranges, the temperature in a lower portion of second distillation column 500 ranges from 40° C. to 165° C., e.g., from 50° C. to 160° C., from 60° C. to 155° C., from 70° C. to 150° C., from 80° C. to 140° C., from 90° C. to 135° C., from 100° C. to 140° C., from 110° C. to 135° C., or from 115° C. to 130° C. In terms of upper limits, the temperature in a lower portion of this distillation column is less than 165° C., e.g., less than 160° C., less than 155° C., less than 150° C., less than 145° C., less than 140° C., less than 130° C., less than 125° C., or less than 120° C.

For operating condition (ii), a water amount in a lower portion of the second distillation column 500 is 0.3 wt. % or more, e.g., 0.4 wt. % or more, 0.5 wt. % or more, 0.6 wt. % or more, 0.8 wt. % or more, 1 wt. % or more, 1.5 wt. % or more, or 2 wt. % or more. In terms of ranges, the water amount in a lower portion of this distillation column ranges from 0.3 wt. % to 20 wt. %, e.g., from 0.5 wt. % to 18 wt. %, from 0.8 wt. % to 16 wt. %, from 1 wt. % to 15 wt. %, from 1.5 wt. % to 14 wt. %, from 2 wt. % to 12 wt. %, from 3 wt. % to 10 wt. %, from 4 wt. % to 9 wt. %, or from 5 wt. % to 9 wt. %. The water amount in the lower portion of the second distillation column 500 is less than 20 wt. %, e.g., less than 18 wt. %, less than 15 wt. %, less than 10 wt. %, less than 5 wt. %.

For operating condition (iii), the acetic acid amount in the lower stream on weight percentage basis is greater than the acetic acid amount in the first mixture. The acetic acid in the first mixture may be transferred to the lower steam predominantly than the upper stream. In some embodiments, acetic acid in lower stream is not more than 3 wt. %, e.g., not more than 2.8 wt. %, not more than 2.5 wt. %, not more than 2.2 wt. %, not more than 2 wt. %, or not more than 1.8 wt. %. To achieve these acetic acid amount, more than 50% of the acetic acid in the first mixture is transferred to the lower stream, e.g., more than 60%, more than 70%, more than 80% or more than 90%.

A distillation step that satisfies any of operating conditions (i)-(iii) can control the 1,1 dimethoxyethane amount in the lower stream to less than or equal to 0.03 wt. %, based on the total weight of the lower stream, e.g., less than or equal to 0.025 wt. %, less than or equal to 0.02 wt. %, less than or equal to 0.01 wt. %, or less than or equal to 0.005 wt. %. In some embodiments, the 1,1 dimethoxyethane amount in the lower stream ranges from 0.001 wt. % to 0.03 wt. %, based on the total weight of the lower stream, e.g., 0.001 wt. % to 0.025 wt. %, 0.004 wt. % to 0.02 wt. %, or 0.008 wt. % to 0.015 wt. %.

In some embodiments, the first mixture (e.g., the first overhead stream 302 from the first distillation column 300 or derivative streams therefrom) to the second distillation column 500 comprises a methanol amount of less than or equal to 2 wt. %, based on the total weight of the feed mixture, e.g., less than or equal to 1.5 wt. %, less than or equal to 1 wt. %, less than or equal to 0.5 wt. %, less than or equal to 0.1 wt. %, less than or equal to 0.05 wt. %, less than or equal to 0.01 wt. %, or less than or equal to 0.0005 wt. %. In terms of ranges, the feed mixture to second distillation column 500 comprises a methanol amount from 0.0001 to 2 wt. %, e.g., from 0.0005 to 1.5 wt. %, from 0.01 to 1 wt. %, from 0.05 to 0.5 wt. %, or from 0.1 to 0.3 wt. %.

As mentioned above, due to the lower amount of 1,1-dimethoxyethane in the lower portion of the second distillation column 500 at the operating conditions described herein, more acetaldehyde distributes to the upper portion of the column to form a concentration zone of PRC's. In some embodiments, the first overhead stream 302 (e.g., the condensate, the aqueous phase, the organic phase, or combinations thereof) is fed to the second distillation column 500 and PRC's are effectively extracted by adding an extractant (e.g., water) to the concentration zone in the second distillation column 500. The extractant may be suitable composition for extracting acetaldehyde from the first mixture. For ease of processing, the extractant may also be separable from methyl iodide using a low energy technique including liquid-liquid separation and/or membrane separation. The extractant may comprise extracting water, a mixed solvent or a water-soluble organic solvent (glycol, glycerin, acetones, ethers, and/or esters). Introducing water is advantageous to maintain the extracting mixture in a liquid-liquid separation state and thus, the extractant is made to comprise not less than 80 wt. % water, e.g., not less than 90 wt. % water, or not less than 95 wt. % water. In one embodiment, to prevent excess formation, the extractant practically does not comprise methanol, or other mono-alcohols. The first (feed) mixture is effectively distillated in the upper stream (second overhead stream 502 or sidecut stream 504) which contains a high amount of at least methyl iodide (in particular, high amounts of both at least methyl iodide and PRC's).

The first overhead stream 302 (or a derivative stream thereof) is distilled in the second distillation column 500 to form an upper stream and a lower stream. The upper stream may comprise at least one of a second overhead stream 502 or a sidecut stream 504. In the second distillation column 500, an extractant (e.g., water) may be added to the second distillation column 500 via line 524 to extract PRC's from a mass composition zone of PRC's. The extractant preferentially extracts PRC's than methyl iodide from the mass composition zone to form an extraction mixture. The extraction mixture (containing the PRC's extracted from the mass composition zone) falling from the concentration zone can be withdrawn as the sidecut stream 504. In some embodiments, the ratio of acetaldehyde relative to methyl iodide in the sidecut stream 504 is higher than that in the first overhead stream 302 and is higher than that in the lower stream 506. The process efficiently separates PRC's and methyl iodide from each other by extractive distillation of PRC's in the coexistence of methyl acetate and/or acetic acid.

At the operating conditions described herein for the second distillation column 500, less 1,1-dimethoxyethane is produced in the lower portion of the column. In some embodiments, the weight ratio of 1,1-dimethoxyethane mass composition in the lower stream to overhead stream is from 100:1 to 10:1, e.g., from 95:1 to 15:1, from 90:1 to 20:1, from 80:1 to 25:1, from 75:1 to 30:1, from 70:1 to 40:1, or from 60:1 to 50:1. In some embodiments, the weight ratio of 1,1-dimethoxyethane mass composition in the lower stream to the sidecut is from 100:1 to 10:1, e.g., from 95:1 to 15:1, from 90:1 to 20:1, from 80:1 to 25:1, from 75:1 to 30:1, from 70:1 to 40:1, or from 60:1 to 50:1.

In some embodiments, the first mixture to the second distillation column 500 may comprise a total mass composition of PRCs (e.g., acetaldehyde) from 0.05 to 50 wt. %, from 0.05 to 10 wt. %, from 0.1 to 5 wt. % or from 0.1 to 1 wt. %. Thus, a targeted amount of PRCs may be separated from first mixture. The first mixture may be derived from first overhead stream 302, or a portion thereof, may also contain other components, including but not limited to $C_1$-$C_{12}$ alkyl iodides, acetic acid, methyl acetate, water, and/or methanol, and others. When a mixed composition is derived from portions of the aqueous and organic phases, the first mixture may have a mass composition of $C_1$-$C_{12}$ alkyl iodides (methyl iodide) that is from 2.5 wt. % to 90 wt. %, e.g., from 10 wt. % to 85 wt. %, or from 20 to 70 wt. %, and a mass composition of water that is from 0.5 wt. % to 90 wt. %, e.g., from 1 wt. %, to 90 wt. %, or from 1.5 wt. %, to 85 wt. %, in addition to PRCs. A representative $C_1$-$C_{12}$ alkyl iodide is methyl iodide. In one embodiment, the amount of $C_1$-$C_{12}$ alkyl iodides is greater than the amount of water. Importantly, in the first mixture there is a composition where the mass compositions of PRCs, $C_1$-$C_{12}$ alkyl iodides, and water can be selected from a wide range disclosed herein. The composition in first mixture may be a homogeneous liquid or a mixture of aqueous and organic phases. The composition first mixture may also comprise methyl acetate in an amount up to 30 wt. %, e.g., from 0.1 to 28 wt. %, or from 1 to 20 wt. %, acetic acid in an amount up to 25 wt. %, e.g., from 0.01 to 12 wt. %, or from 0.5 to 7.5 wt. %, and dimethyl ether in an amount up to 1 wt. %, e.g., from 0.001 to 1 wt. %, or from 0.004 to 0.8 wt. %.

In addition to these components, the first mixture also may comprise methanol. The methanol may be unreacted methanol, or methanol obtained through secondary reactions in during the separation and/or distillation process. In one embodiment, the methanol mass composition in the first mixture may be less than or equal to 2 wt. %, e.g., less than or equal to 1.8 wt. %, less than or equal to 1.5 wt. %, less than or equal to 1.1 wt. %, less than or equal to 1.0 wt. %, or less than or equal to 0.5 wt. %.

As mentioned above, in the second distillation column 500, the first overhead stream 302 (first mixture) is distilled to form a mass composition zone (a zone with high mass compositions of PRC's (in particular, acetaldehyde and methyl iodide) in the upper position of the second distillation column 500. For example, the mass composition zone of PRC's may form in a portion of the second distillation column 500 above the feed line of the first mixture. An extractant can be added to the mass composition zone via line 524 to extract PRC's (in particular, acetaldehyde) preferentially to other components in the mass composition zone (e.g., methyl iodide), and an extraction mixture falling from the mass composition zone is withdrawn as a sidecut stream 504 from the second distillation column 500. The extraction mixture has a PRC (in particular, acetaldehyde) mass composition significantly higher than the first overhead stream 302 fed to the second distillation column 500. Withdrawing the extraction mixture as the sidecut stream 504 allows PRC's to be separated or removed effectively.

In some embodiments, the second distillation column 500 has more than 10 (actual) stages, e.g., more than 15 stages, more than 20 stages, more than 25 stages, or more than 30 stages. For example, for a plate distillation column having the total actual number of stages (or plates) of 43, the feed plate to which the first overhead stream 302 is fed may be about the 1st to the 20th plate, e.g., about the 2nd to the 15th plate, or about the 4th to the 10th plate from the bottom of the distillation column. For example, for a plate distillation column having the total actual number of stages (or plates) of 10, the feed plate to which the first mixture is fed may be about the 1st to the 7th plate, e.g., about the 1st to the 5th plate, or about the 1st to the 3rd plate from the bottom of the distillation column.

In some embodiments, the position (feed port, or feed plate or tray) at which the first mixture (e.g., first overhead stream 302 or an aqueous/organic phase) is fed to the second distillation column 500 may vary. In some embodiments, assuming that the height level of the distillation column is "1", the first overhead stream 302 may, for example, be fed at a height level of about 0.01/1 to 0.7/1, e.g., about 0.01/1 to 0.5/1, about 0.03/1 to 0.45/1, about 0.04/1 to 0.4/1, or about 0.05/1 to 0.35/1 from the bottom.

In some embodiments, the extractant can usually be added to the upper part of the second distillation column 500. In some embodiments, the extractant can be added to the uppermost plate of the column, or between the top of the column and a plate that is positioned at least one plate upper than the feed part or feed tray of the first mixture. Assuming that the second distillation column 500 has the total number of plates of 100, the feed plate of the extractant may be a plate at or near the top of the second distillation column 500, for example, about the 0th to the 50th plate, e.g., about the 1st to the 25th plate, about the 1st to the 20th plate, about the 1st to the 15th plate), or about the 1st to the 10th plate from the top of the distillation column. In other words, assuming that the height level of the distillation portion of the distillation column is "1", the extractant may, for example, be fed at a height level of about 0/1 (the top of the column) to 0.5/1, e.g., about 0.01/1 to 0.25/1, about 0.01/1 to 0.2/1, about 0.01/1 to 0.15/1, or about 0.01/1 to 0.1/1 from the top of the column.

In order to increase the extraction efficiency by counter-currently adding the extractant to the rising vapor or evaporation fraction, the extractant may usually be added to the uppermost plate of the second distillation column 500. In order to increase the extraction efficiency, the extractant can be added in a droplet form, in particular, may be added by spraying or sprinkling. The extractant may have a temperature of, for example, about 0 to 60° C., e.g., about 10 to 50° C., about 20 to 40° C., or about 15 to 25° C. The extractant may be added as an extractant warmed or heated, e.g., heated to about 30 to 150° C., about 50 to 110° C., or in the form of vapor (including superheated vapor).

The extractant is capable of extracting PRC's (in particular, acetaldehyde) preferentially to other components in the mass composition zone (e.g., methyl iodide). The extractant is preferably separable from the methyl iodide phase by liquid-liquid separation. Specifically, the extractant can separate the extraction mixture into an upper phase and a lower phase. In particular, the extractant may include an aqueous extractant containing at least water, for example, water, and a mixed solvent containing water and a water-soluble organic solvent, e.g., an alcohol such as methanol, a glycol such as ethylene glycol, a polyhydric alcohol such as glycerin, acetone, an ester, and an ether.

The extractant may contain water and at least one component selected from the group consisting of PRC's, methyl iodide, acetic acid, methyl acetate, dimethyl ether, and a component present in the process (all components including the impurities described above). Such an extractant may be an aqueous solvent produced in the process, e.g., an aqueous phase produced in the liquid-liquid separation step of the first overhead stream, an aqueous process stream such as the extracts produced in the second liquid-liquid separation step (e.g., an acetaldehyde-containing aqueous process stream), and other acetaldehyde-containing aqueous process streams, e.g., an aqueous phase formed by extracting PRC's with water. The extractant may also include an aqueous solution (for example, an aqueous solution containing acetaldehyde and methyl iodide) obtainable by absorption-treating an off-gas with water, the off-gas being produced from the process.

In some embodiments, the first overhead stream 302 (or the condensate, the aqueous phase, the organic phase, or combinations thereof) is fed to the second distillation column 500 and is distilled without supply (or addition) of water (other than water in the reflux to the column) to the second distillation column 500. When distilling the first overhead stream 302, a portion of water in the first overhead stream 302 distributes to an upper position than the feed port of the second distillation column 500 to form a second mixture (for example, a biphasically separable second mixture by condensation) having an increased amount of water by transfer or distribution of water.

In some embodiments, the second mixture can be withdrawn as a second overhead stream 502. The lower stream 506 may have a decreased amount of water than the second overhead stream 502 and is withdrawn from a lower position than the feed port. Specifically, the water in the first overhead stream 302 is transferred to the second overhead stream 502 as the upper stream predominantly than the lower stream 506. In this way, the second overhead stream 502 has a significantly higher PRC's (e.g., acetaldehyde) amount than the first overhead stream 302 or first mixture fed to the second distillation column 500. The second overhead stream 502 may be condensed and biphasically separated to form an aqueous phase having further effectively concentrated PRC's.

The second distillation column 500 can be operated under specific conditions to transfer water in the first overhead stream 302 predominantly to the second overhead stream 502 than the lower stream 506. For example, operating the second distillation column 500 at the specific operating conditions described herein, a zone having a high water amount is formed in the distillation column. In some embodiments, a zone having a high concentration of PRC's and methyl iodide at an upper position than the feed port of the second distillation column 500 and allows at least a portion of water in the first mixture to distribute to the concentration zone. In this process, a mixture falling from the concentration zone may be withdrawn as a sidecut stream 504. A relatively lower amount of extractant may be used when the PRCs, including acetaldehyde, are extracted into the upper stream (second overhead stream 502 or sidecut stream 504) as opposed to the lower stream 506. For example, the flow rate ratio (on a weight basis) of the extractant in line 524 relative to first mixture (such as the lines 410 and/or 412) may range from 0.0001/100 to 100/100, e.g., 0.001/100 to 50/100, 0.0001/100 to 20/100, 0.001/100 to 10/100, 0.01/100 to 8/100, or 0.1/100 to 5/100. In using an extractive distillation step in the second distillation, PRC's and the $C_1$-$C_{12}$ alkyl iodides may be processed in an efficient manner that reduces the energy requirements.

The internal temperature of the second distillation column 500 of the second distillation step depends on an internal pressure thereof. At the internal pressure of an atmospheric pressure, the second distillation column 500 may have a column top temperature of, for example, about 15 to 120° C., e.g., about 18 to 100° C., about 20 to 90° C., e.g., about 20 to 80° C., about 20 to 70° C., or about 25 to 70° C. In the second distillation step, other distillation conditions (e.g., the number of theoretical stages of the distillation column, and the reflux ratio) may be the same as those in the first distillation step. The reflux ratio (reflux:distillate) of the second distillation column 400 is from 1:20 to 20:1, e.g., from 1:15 to 15:1, or from 5:1 to 10:1.

The internal pressure of the second distillation column 500 may influence the formation of acetals in the distillation column. For example, fluctuations in the internal pressure of the second distillation column 500 can be controlled to suppress acetal formation. In some embodiments, the second distillation column 500 may be equipped with a pressure control device to control pressure in the distillation column. The pressure in the distillation column (e.g., in the top portion or bottom portion of the column) can be controlled by introducing an inert gas or an off-gas into the column and/or by discharging a non-condensable gas from the distillation column. In some embodiments, the internal pressure of the distillation column (e.g., the top or bottom portion of the column) in the second distillation step may be, for example, about 0.1 to 0.7 MPa in terms of absolute pressure, for example, about 0.01 to 0.6 MPa, preferably about 0.13 to 0.4 MPa, and about more preferably 0.15 to 0.35 MPa. In some embodiments, the internal pressure of the distillation column is less than or equal to 0.7 MPa, e.g., less than 0.6 MPa, less than 0.5 MPa, less than 0.4 MPa, less than 0.3 MPa or less than 0.2 MPa. The second distillation step can control an internal pressure of a distillation column to form a second overhead rich in acetaldehyde and methyl iodide. The second overhead stream 502 may have a temperature at an atmospheric pressure of 15 to 110° C., e.g., 18 to 90° C., 20 to 80° C., or 20 to 70° C.

In some embodiments, the second distillation column 500 is provided with a collector tray (plate) 501, which may be referred to as a hat tray or chimney tray, to allow the good vapor distribution to the upper zone from the first mixture and the holding of the whole amount of the extraction mixture to be taken off as sidecut stream 504. Any suitable design for the collector tray 501 may be used with the embodiments described herein. The collector tray 501 is practically located where the sidecut stream 504 is taken and thus the extractant 524 is be added above the collector tray 501. This allows the falling liquid from the upper portion of the second distillation column 500 to be received on collector tray 501.

As shown in FIG. 2, second distillation column 500 separates the components of first mixture (from the first overhead stream) 302 at a first location of the second distillation column 500 through extractive distillation. It should be understood for purposes of the disclosure contained herein that from 302 in FIGS. 2-4 may include the first overhead stream 302 or any portion thereof (aqueous phase or organic phase) as the first mixture. In one embodiment, the feed line may be extracted with an extractant 524 that is introduced in an upper zone of the second distillation column 500 is above the first location. In some embodiments, the second overhead 502 is condensed and a distillate portion is used as the second mixture for removing PRCs. In the embodiment shown in FIG. 2, the composition of the second overhead 502 may be phase separable in overhead receiver 520 (e.g., decanter) into an aqueous phase 523 and an organic phase 522. The organic phase 522 may be enriched in methyl iodide and deficient in water, while the aqueous phase 523 may contain useful amounts of PRCs and water. In some embodiments, to remove acetaldehyde aqueous phase 523 may be combined with sidecut stream 504 and fed to vessel 600 or aqueous phase 523 may be fed to vessel

600 separately. In still further embodiments, a portion of the aqueous phase 523 may be used as the reflux on the second distillation column 500, while the organic phase 522, which may also contain amounts of acetaldehyde is fed to vessel 600.

Depending on the mixed composition in the first mixture, acetaldehyde may be effectively extracted into the second overhead 502, notwithstanding that presence of methyl acetate and/or acetic acid, which tend to have an affinity with both PRCs (including acetaldehyde) and $C_1$-$C_{12}$ alkyl iodides (including methyl iodide). In one embodiment, the amount of acetaldehyde in the upper portion of the column (including the second overhead 502 and/or side cut 504) is from 5 to 1000 times more than the amount in the first mixture on a weight basis, e.g., from 10 to 500 times or from 20 to 300 times.

In some embodiments, the second overhead stream 502 and/or the sidecut stream 504 is condensed. The condensate can be refluxed at the top portion of the second distillation column 500. In some embodiments, there may be a distillate that is removed from the top of the second distillation column 500, but generally the condensed portion of the second overhead stream 502 is refluxed. The second overhead stream 502 exits the second distillation column 500 at a temperature ranging from 15° C. to 120° C. and the condenser (or plurality of condensers as needed) may condense the second overhead stream 502 to a temperature lower than the boiling point of methyl iodide. The condensed liquid 510 is accumulated in an overhead receiver 520 and refluxed via line 522. To maintain extractive conditions, line 522 may enter second distillation column 500 between the location of the extractant 524 and withdrawing location of sidedraw 504 (e.g., above collector tray 501). This reflux can be used to prevent excess amounts of extractant and namely water, from being presence in the overhead 502.

In a lower portion of second distillation column 500 a miscible solvent may be directly or indirectly fed to the column. This solvent is miscible with a process stream containing methyl iodide. The miscible solvent may be at least one component selected from the group consisting of water, acetic acid, methyl iodide, and methanol. When added, the miscible solvent may be not more than 30% relative to the amount of the sidecut stream 504 withdrawn from collector tray 501, e.g., not more than 15%, or not more than 10%.

As shown in FIG. 2, the sidecut stream 504 may be collected in vessel 600. Vessel 600 may be a buffer tank or may be a liquid-liquid separation vessel capable of receiving the sidecut stream 504 and separating the sidecut stream 504 into phases. In some embodiments, vessel 600 separates the liquid-liquid separable sidecut stream 504 into an aqueous phase 602 and an organic phase 604. PRCs, including acetaldehyde, distributes more favorably into the aqueous phase 602 than organic phase 604. In addition, the extractant is more favorably separated into aqueous phase 602, and the extractant may be recovered through subsequent processing of the aqueous phase, although it is not necessary to recover the extractant. The organic phase may be returned to second distillation column 500, which maintain operation under at least one of conditions (i) to (iii), or combined with the lower stream 506 and is returned to the reactor 100. In addition, it is desirable to have reduced amounts of methyl iodide in the aqueous phase 602 so that the acetaldehyde may be discharged without further processing.

In one embodiment, the vessel 600 separates the side cut 504 into an aqueous phase 602 and organic phase 604. The mass flow ratio of the aqueous phase 602 and the organic phase 604 may be from 1:1000 to 1:1 (aqueous phase to organic phase), e.g., from 1:900 to 1:10 or from 1:650 to 1:100. On balance, the aqueous phase 602 may be the smaller stream, based on the mass flow, than the organic phase 604. The organic phase 604 is deficient in the extractant and may be returned to the second distillation column 500.

The aqueous phase 602 has higher PRCs (acetaldehyde) amount than the organic phase 604, and the aqueous phase 602 may have a higher amount of PRCs than $C_1$-$C_{12}$ alkyl iodides (methyl iodide). Using acetaldehyde and methyl iodide as representatives, the aqueous phase 602 may have a ratio of former to latter, on a weight, from 2:1 to 60:1, e.g., from 3:1 to 45:1, from 3:1 to 30:1, or from 4:1 to 20:1. The composition of aqueous phase 602 comprises a PRC (acetaldehyde) mass composition from 1 to 50 wt. %, e.g., from 5 to 45 wt. % or from 10 to 35 wt. %, water mass composition from 40 to 95 wt. %, e.g., from 50 to 90 wt. %, or from 60 to 75 wt. %, $C_1$-$C_{12}$ alkyl iodides (methyl iodide) mass composition from 0.01 to 15 wt. %, e.g., from 0.1 to 10 wt. %, or from 0.5 to 6 wt. %, methyl acetate mass composition from 0.1 to 25 wt. %, e.g., from 0.5 to 20 wt. %, or from 0.5 to 10 wt. %, acetic acid mass composition from 0 to 5 wt. %, e.g., from 0.01 to 2.5 wt. %, or from 0.05 to 1 wt. %, methanol mass composition from 0 to 2.5 wt. %, e.g., from 0.01 to 2.1 wt. %, or from 0.05 to 2 wt. %, acetal mass composition from 0 to 2.5 wt. %, e.g., from 0.01 to 1.7 wt. %, or from 0.05 to 1.5 wt. %, and dimethyl ether mass composition from 0 to 1.2 wt. %, e.g., from 0.01 to 0.8 wt. %, or from 0.05 to 0.5 wt. %.

The organic phase 604 may be returned to second distillation column 500 below the collector tray 501. In one embodiment, the composition of organic phase 604 comprises a $C_1$-$C_{12}$ alkyl iodides (methyl iodide) mass composition from 0.1 to 90 wt. %, e.g., from 5 to 85 wt. %, or from 10 to 80 wt. %, methyl acetate mass composition from 0.1 to 30 wt. %, e.g., from 0.5 to 20 wt. %, or from 0.5 to 10 wt. %, PRC (acetaldehyde) mass composition from 0.01 to 15 wt. %, e.g., from 0.5 to 10 wt. % or from 0.5 to 5 wt. %, acetic acid mass composition from 0 to 5 wt. %, e.g., from 0.01 to 2.5 wt. %, or from 0.05 to 1 wt. %, water mass composition from 0.01 to 5 wt. %, e.g., from 0.05 to 4 wt. %, or from 0.5 to 3.5 wt. %, methanol mass composition from 0 to 2.5 wt. %, e.g., from 0.01 to 2.1 wt. %, or from 0.05 to 2 wt. %, acetal mass composition from 0 to 2.5 wt. %, e.g., from 0.01 to 1.7 wt. %, or from 0.05 to 1.5 wt. %, and dimethyl ether mass composition from 0 to 1.2 wt. %, e.g., from 0.01 to 0.8 wt. %, or from 0.05 to 0.5 wt. %. The organic phase 604 may also comprise methanol and the additional methanol in the organic phase 604 returned to the second distillation column 500 may increase the rate of formation acetal (1,1-dimethoxyethane). To control acetal formation, when the organic phase 604 is returned to the second distillation column 500 and contains methanol, the total methanol mass composition of the first mixture and organic phase is less than or equal to 2 wt. %, e.g., less than or equal to 1.5 wt. %, less than or equal to 1 wt. %, less than or equal to 0.5 wt. % or less than or equal to 0.25 wt. %. When the organic phase 604 contains more than 2 wt. % methanol, the organic phase 604 may be combined with lower stream 506 without feeding the organic phase 604 to the second distillation column 500. To operate with effectively, in one embodiment the lower stream 506 contains a significant portion of the methyl iodide from feed stream 302, in particular when feed stream 302 comprises portion of the organic phase 404. The lower stream 506 of distillation column 500 contains useful methyl iodide that is returned to the reactor 100. To achieve efficient production, the distillation column removes 60 to 99.9% of the methyl iodide in the feed stream 302 into the lower stream 506, e.g., from 75 to 99.5% or from 80 to 99.1%. Successful removal of methyl iodide provides a lower stream 506 having a mass composition of $C_1$-$C_{12}$ alkyl iodides (methyl iodide) from 10 to 90 wt. %, e.g., from 15 to 85 wt. %, or from 20 to 80 wt. %. However, in doing so, this increases the 1,1-dimethoxy-ethane return to the reactor. To overcome these shortcomings and to efficient use the lower stream 506, the water mass compositions are maintained at sufficient levels to transform or convert the 1,1-dimethoxyethane.

The lower stream 506 may be withdrawn at a temperature from 30° C. to 160° C., e.g., 35° C. to 120° C., or 40° C. to 100° C.

Supplementary Acetaldehyde Removal

Although acetaldehyde, including other PRCs, are removed from the feed stream 302 to the second distillation column 500, it may be desirable to remove or reduce acetaldehyde through supplementary processing and recover either useful organic components and/or extractant. There are several available methods for achieving such supple-mentary removal of acetaldehyde. For the purposes of present invention, these supplementary removal processes if used at all, can vary depending on the requirements on the processing facility. One aspect of supplemental acetalde-hyde removal is that the process should not increase the 1,1-dimethoxyethane mass composition in the lower stream 506.

In one embodiment, acetaldehyde may be removed or reduced by purging the upper stream (e.g., the second overhead 502 or sidecut stream 504) from the second distillation column 500 from the process. This may be done with an upper stream that contains very low amounts of methyl iodide, in particular amounts that are less than 1 wt. %, e.g., less than 0.5 wt. %. When the upper stream contains higher amounts of methyl iodide, it may be desirable to avoid purging of the second mixture by employing a supple-mental acetaldehyde removal process.

In another embodiment, there may be a second extraction step of the upper stream in an extractor having no stages or distillation column having stages. For this supplemental acetaldehyde removal process, the second extraction uses a secondary extractant (additional water) and may yield an extractant containing the acetaldehyde and a raffinate con-taining the methyl iodide. This allows the raffinate to be recovered and the extractant to be further disposed of or purged. Under this arrangement, the second extraction may be positioned as a consecutive stage with the second distil-lation column 500. There may be a condenser/chiller between the extraction stages, i.e., the second distillation column 500 and extractor. The temperature of the upper stream using the condenser/chiller may be from 10° C. to 80° C., e.g., from 12° C. to 65° C. or from 13° C. to 45° C.

Figure 3:
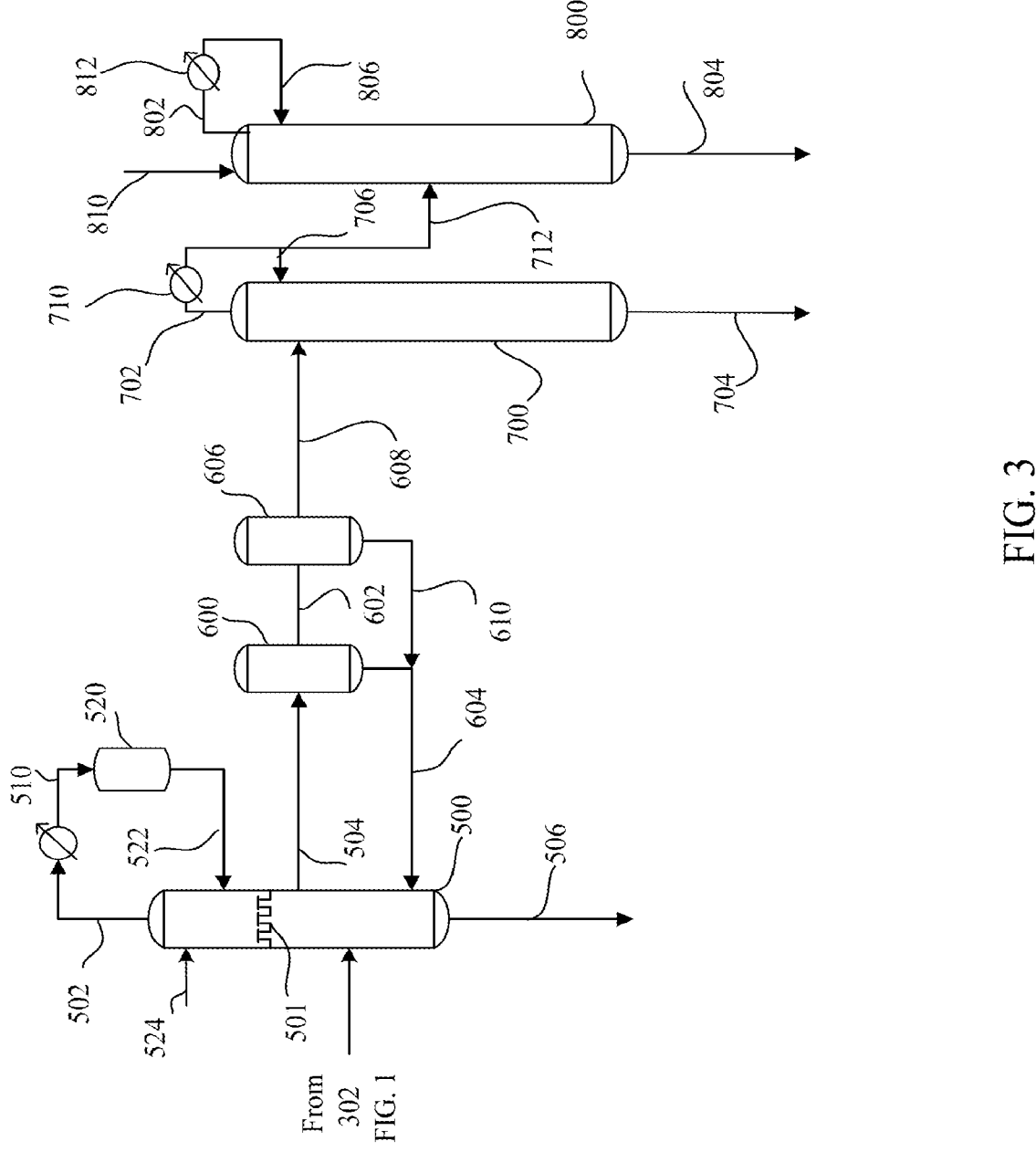
FIG. 3 illustrates a schematic flow diagram of a by-product removal system in accordance with some embodiments of the present invention.

FIG. 3 shows one embodiment of a supplemental acetal-dehyde removal process. As mentioned above, the first mixture to the second distillation column 500 is represented as the first overhead 302, but it should be understood that the first mixture may comprise a portion of the first overhead 302, including the liquid-liquid separated upper and lower streams described above. After the first mixture is distilled and/or extracted in second distillation column 500, the second mixture is withdrawn as side cut stream 54 from second distillation column 500 and introduced to vessel 600.

The second overhead 502 is condensed and the condensed portion 510 is refluxed via line 522. Water is used an extractant 524 and introduced to the top of the second distillation column 500. The lower stream 506 is removed from the bottom of second distillation column 500 and is recycled to a vessel containing at least 1.5 wt. % or more of water to transform 1,1-dimethoxyethane contained therein. The organic phase 604 from vessel 600 is recycled to a lower portion of second distillation column 500. The organic phase 602 being rich in methyl iodide as compared to the second mixture, may be recycled to a position lower than the position for withdrawing the side cut stream 504, e.g., lower than the collector tray 501.

The phase separated sidecut stream 504 contains rela-tively more acetaldehyde in the aqueous phase 602 than the organic phase 604. Aqueous phase 602, due to its water content, may be a suitable extracting mixture for second distillation column 500 and a portion thereof may be recycled as the extractant 524. This recycle portion may comprise the whole extractant or may be combined with additional sources of water to comprise a portion of the extractant. In one embodiment, aqueous phase 602 is not used as an extractant and may be have a closable valve or may be removed from the process.

Similar to the relatively high temperature of the sidecut stream 504 (second mixture), the aqueous phase 602 from vessel 600 may be cooled by passing through a condenser (cooler) prior to be collected in decanter 606. Cooling water or process water may be used as the coolant. The tempera-ture of the aqueous phase 602 may be from −5° C. to 60° C., e.g., from 0° C. to 30° C. or from 3° C. to 20° C.

In the decanter 606, there may be a residual amount of methyl iodide that is separable by a liquid-liquid separation into a residual stream 610. The residual stream 610 contains more methyl iodide than aqueous phase 608. The residual stream 610 (a heavy phase rich in methyl iodide or a lower phase) formed in the decanter 606 is recycled to the second distillation column 500 by either being combined with the organic phase 604 of vessel 600 or being independently added to the second distillation column 500 below the collector plate 501. Although residual stream 610 may bypass the second distillation column 500 and can be returned to reactor 100 with lower stream 506, it is preferred to first reduce impurities in residual stream 610 prior to returning to reactor 100. To prevent phase issues, it is not advisable to introduce residual stream 610 back into vessel 600.

Decanter 606 also yields a liquid stream 608. The liquid stream 608 contains the targeted acetaldehyde to be removed. The mass flow ratio of the liquid stream 608 and the residual stream 610 may be from 1:500 to 1:0.5 (liquid to residual), e.g., from 1:400 to 1:1 or from 1:375 to 1:10. Despite the relatively smaller stream, the liquid stream 608 contains a useful amount of acetaldehyde. The acetaldehyde mass composition in liquid stream 608 based on amount may be more than 2× (two times) the amount in residual stream 610, e.g., more than 3× or more than 4×.

Although the liquid stream 608 may be disposed of to reduce the acetaldehyde amount (e.g., purged from the process), there may be processes which seek to further retain methyl iodide and/or the extractant (water) used for the extracting mixture. Thus, the liquid stream 608, or a portion thereof, may be further subjected to separation using a third distillation column 700. In such a distillation, third distilla-tion column 700 yields a third overhead stream 702 con-taining acetaldehyde in an amount from 1 to 99 wt. % and methyl iodide in an amount from 0.1 to 30 wt. %, and a bottoms stream 704 containing the extractant as the main component in an amount of not less than 10 wt. %, and methyl iodide in an amount of not more than 1 wt. % (provided that, each stream, including impurities, has a total amount of 100% by weight). A portion of the bottoms stream 704 may be used as the extractant via line 524 and returned to second distillation column 500. In other embodiment, bottoms stream 704 may be removed or discharged from the process.

The third distillation column 700 may have a column top pressure (absolute) from 100 to 500 kPa, e.g., 115 to 375 kPa and 125 to 250 kPa. To effectively separate the overhead, the third distillation column 700 at atmospheric pressure has a temperature at the column top from 10 to 90° C., e.g., from 15 to 80° C. or 20 to 60° C., and/or a column bottom temperature from 70 to 170° C., e.g., from 80 to 160° C. or from 90 to 150° C. The number of stages (plates) in the third distillation column 700 may be a sufficient number for separation, for example, from 1 to 50 plates, e.g., from 2 to 45 plates or from 3 to 30 plates. The reflux ratio (reflux: distillate) of the third distillation column 700 is from 1:20 to 20:1, e.g., from 1:15 to 15:1, or from 5:1 to 10:1.

The third overhead stream 702 or a distillate thereof contains more acetaldehyde and has a lower methyl iodide amount than the second mixture. In one embodiment, the composition of third overhead stream 702 comprises a PRC (acetaldehyde) mass composition from 45 to 99 wt. %, e.g., from 50 to 99 wt. % or from 60 to 98 wt. %, $C_1$-$C_{12}$ alkyl iodides (methyl iodide) mass composition from 0.1 to 30 wt. %, e.g., from 0.5 to 25 wt. %, or from 1 to 20 wt. %, methyl acetate mass composition from 0.1 to 25 wt. %, e.g., from 0.5 to 20 wt. %, or from 0.5 to 12 wt. %, acetic acid mass composition from 0 to 5 wt. %, e.g., from 0 to 1.5 wt. %, or from 0 to 1 wt. %, water mass composition from 0 to 5 wt. %, e.g., from 0 to 2.5 wt. %, or from 0.01 to 2 wt. %, methanol mass composition from 0 to 2.5 wt. %, e.g., from 0.01 to 2.1 wt. %, or from 0.05 to 2 wt. %, acetal mass composition from 0 to 2.5 wt. %, e.g., from 0.01 to 1.7 wt. %, or from 0.05 to 1.5 wt. %, and dimethyl ether mass composition from 0 to 1.2 wt. %, e.g., from 0.01 to 0.8 wt. %, or from 0.05 to 0.5 wt. %. In one embodiment, the third overhead stream 702 has a ratio (based on weight) of methyl iodide relative to acetic acid is that higher than this ratio in feed to the third distillation column 700. In addition or separately, the third overhead stream 702 may have a ratio (based on weight) of methyl iodide relative to methyl acetate is that higher than this ratio in feed to the third distillation column 700.

Third overhead stream 702 has a temperature at atmospheric pressure from 15 to 100° C., from 20 to 90° C., or from 35 to 75° C. A conventional condenser/cooler 710 may be used to condense the third overhead stream 702 to cool the third overhead stream 702 to a temperature of not more than 60° C., e.g., not more than 45° C. or not more than 30° C. A portion of the condensate can be refluxed to the third distillation column via line 706.

In one embodiment, when the extractant 524 added to the second distillation column 500 is water, the bottoms stream 704 can function as the extractant because it contains water as the main component. In addition to the main component, the bottoms stream 704 may contain methyl acetate and lower amounts of acetic acid, methanol, dimethyl ether, methyl iodide, and/or acetaldehyde. This allows a portion of bottoms stream 704, or the whole bottoms stream 704, to be used as the extractant 524 to second distillation column 500. The bottoms stream 704 may have a water mass composition from 85 to 99.99 wt. %, e.g., from 90 to 99.98 wt. % or from 92 to 99 wt. %. Methyl acetate may be retained in the lower part of the third distillation column 700 and is withdrawn in the bottoms stream 704. The mass composition of methyl acetate in the bottoms stream 704 may be from 0.1 to 15 wt. %, e.g., from 0.5 to 10 wt. %, or from 0.7 to 7 wt. %. The other components, when present, are generally in lower individual amounts of not more than 5 wt. %. In one embodiment, the bottoms stream 704 may have a mass composition of acetaldehyde of not more than 1 wt. %, e.g., not more than 0.5 wt. % or not more than 0.3 wt. %, a mass composition of methyl iodide of not more than 1.5 wt. %, e.g., not more than 1 wt. %, or not more than 0.5 wt. %, a mass composition of acetic acid of not more than 5 wt. %, e.g., not more than 1 wt. %, or not more than 0.5 wt. %, a mass composition of methanol of not more than 1 wt. %, e.g., not more than 0.5 wt. %, or not more than 0.1 wt. %, and/or a mass composition of dimethyl ether of not more than 0.1 wt. %, e.g., not more than 0.01 wt. %, or not more than 0.001 wt. %. Bottoms stream 704 has a temperature at atmospheric pressure from 65 to 165° C., e.g., from 70 to 120° C. or from 85 to 105° C.

Although FIG. 3 shows liquid stream 608 being distilled, in other embodiments, the second mixture and/or aqueous stream 602 may be distilled in the third distillation column 700 without passing through either vessel 600 and/or decanter 606. Separating methyl iodide from acetaldehyde by distillation alone does not fully recover methyl iodide, even though the methyl iodide amount is low in third overhead stream 702. Further, simple distillation may yield marginal or incremental improvements in recovering methyl iodide, thus more effective processing provides attractive benefits for supplemental processing. Extraction with or without distillation may be used as an effective process to enhance recovery of methyl iodide. In one embodiment, a second extractive distillation column may be used to enhance recovery of methyl iodide. As seen in FIG. 3, third overhead stream 702 or a distillate portion thereof, is introduced to fourth distillation column 800 via line 712 that operates as an extractive distillation using a water-containing extractive mixture. Fourth distillation column 800 operates in a manner to obtain an overhead stream 802 enriched in methyl iodide and a bottom stream 804 enriched in acetaldehyde as well as the extractant, being water. At least a portion, including the entire portion, of bottom stream 804 may be recycled or returned to second distillation column 500 as the extracting mixture.

In one embodiment, the fourth distillation column 800 separates an overhead stream 802 from having a ratio (based on weight) of methyl iodide relative to acetaldehyde that is greater than that of the feed in overhead (distillate) stream 702. Overhead stream 802 may be taken as an overhead or a stream near the top of fourth distillation column 80. To maintain recovery, it may be useful to direct the overhead stream 802, either directly or indirectly, to the reactor 100. In some embodiments, a portion of the overhead stream 802 may be introduced to the second distillation column 500, preferably in a lower portion.

For extraction, it is sufficient to add the water-extracting mixture in a counter-current direction at the top of the fourth distillation column 800 via line 810. As described in U.S. Pat. No. 8,859,810, the entire contents and disclosure of which are incorporated by reference, the water-extracting mixture may comprise water, glycols, glycerol, high boiling point alcohols, including mixtures thereof. For the water extractive distillation, the water may have the same temperature as the extractant. The water may be added as a warmed or heated water having the same temperature as the extractant or as a vaporized water (or steam). In one embodiment, the water-extracting mixture 810 has a temperature that is controlled or maintained to be within the range of 0 to 60° C., e.g., 10 to 50° C. or 20 to 40° C. The weight ratio of the flow rate of the water-extracting mixture 810 relative to the flow rate of the overhead stream 802 or a distillate portion thereof [the former/the latter] may range from 1:1000 to 10:1, e.g., from 1:500 to 5:1, 1:100 to 5:1 or 1:4 to 4:1.

In fourth distillation column 800, the overhead stream 802 is cooled and/or condensed, e.g., by passing through a condenser 812 (indirect condenser) and a first portion of the condensate 806 is returned or refluxed to the distillation column 800, while a second portion (not shown) of the condensate is recycled to the reactor 100 in FIG. 1. Bottom stream 804 is a liquid stream and can be withdrawn in the lower portion of distillation column 800, including the bottom or near the bottom, and contains acetaldehyde and the extractant. Owing to the enriched acetaldehyde, bottom stream 804 is purged or discharged outside of the system. A portion of the bottom stream 804 may be used an extractant in either the second distillation column 500 and/or fourth distillation column 800. The overhead stream 802 has a weight ratio of methyl iodide to acetaldehyde that is larger than the methyl iodide to acetaldehyde in liquid stream 804.

The fourth distillation column 800 may have a column top pressure (absolute) from 100 to 500 kPa, e.g., 100 to 400 kPa and 105 to 350 kPa. To effectively separate the overhead, the fourth distillation column 800 at atmospheric pressure has a temperature at the column top from to 90° C., e.g., from 15 to 80° C. or 20 to 60° C., and/or a column bottom temperature from 70 to 170° C., e.g., from 80 to 160° C. or from 90 to 150° C. The number of stages (plates) in the fourth distillation column 800 may be a sufficient number for separation, for example, from 1 to 50 plates, e.g., from 2 to 45 plates or from 3 to 30 plates. The reflux ratio (reflux: distillate) of the fourth distillation column 800 is from 1:20 to 20:1, e.g., from 1:15 to 15:1, or from 5:1 to 10:1.

In one embodiment, the fourth distillation column 800 may have a theoretical stage (or plate) of, for example, less than 50 plates, overhead stream 802 or a condensed portion thereof may have a methyl iodide mass composition from 20 to 80 wt. %, e.g., 30 to 75 wt. % or 40 to 65 wt. %, PRC mass composition from 0.1 to 70 wt. %, e.g., from 0.5 to 65 wt. %, or from 1 to 20 wt. %, methyl acetate mass composition from 0.01 to 15 wt. %, e.g., from 0.05 to 10 wt. %, or from 0.1 to 10 wt. %, acetic acid mass composition from 0 to 5 wt. %, e.g., from 0 to 3 wt. %, or from 0 to 1 wt. %, and water mass composition from 0 to 10 wt. %, from 0 to 8 wt. %, or from 0.01 to 5 wt. %. The mass composition of other organics, such as dimethyl ether and/or methanol, in a mass composition in the overhead stream 802 may be in a minor portion, e.g., not more than 1 wt. % or not more than 0.5 wt. %. Also when the fourth distillation column 800 contains less than 50 plates, the bottom stream 804 may have a PRC mass composition from 1 to 90 wt. %, e.g., from 5 to 80 wt. %, or from 10 to 50 wt. %, water mass composition from 10 to 95 wt. %, from 15 to 90 wt. %, or from 20 to 85 wt. %, methyl iodide mass composition from 0 to 2 wt. %, e.g., 0.01 to 1.5 wt. % or 0.05 to 1 wt. %, methyl acetate mass composition from 0.01 to 15 wt. %, e.g., from 0.05 to 10 wt. %, or from 0.1 to 10 wt. %, acetic acid mass composition from 0 to 5 wt. %, e.g., from 0 to 3 wt. %, or from 0 to 1 wt. %, and a mass composition of organics (dimethyl ether and/or methanol) not more than 3 wt. %, e.g., not more than 1 wt. % or not more than 0.5 wt. %. When the bottom liquid 804 is discharged and/or purged from the process, the acetaldehyde to methyl iodide mass ratio may be from 20:1 to 2000:1, e.g., from 35:1 to 1800:1 or from 50:1 to 1000:1.

In the continuous process to produce acetic acid the process streams, both vapor or liquid streams, may contain various components that are impurities although not described in detail above. These impurities may be formed in the reactor through side reactions. To avoid such impurities it is desirable to suppress the formation of impurities or purge the impurities to prevent build up. The various process stream may contain various amounts formic acid, higher acids, and/or hydrogen iodide.

There may be various configurations of separation process shown in FIG. 3. This includes additional units that supplement or replace the third and/or fourth distillation columns. This allows liquid stream 608 from decanter 606 to bypass third distillation column 700 and is fed into the fourth distillation column 800 or may be fed to one or more extraction vessels. Thus, if necessary, acetaldehyde may be extracted with water from the liquid stream 608 by one or a plurality of water extraction vessel that are provided with a mixer and a settler or by the fourth distillation column 800. In other embodiments, it may not be necessary to use third and/or fourth distillation columns to purify liquid stream 608.

Figure 4:
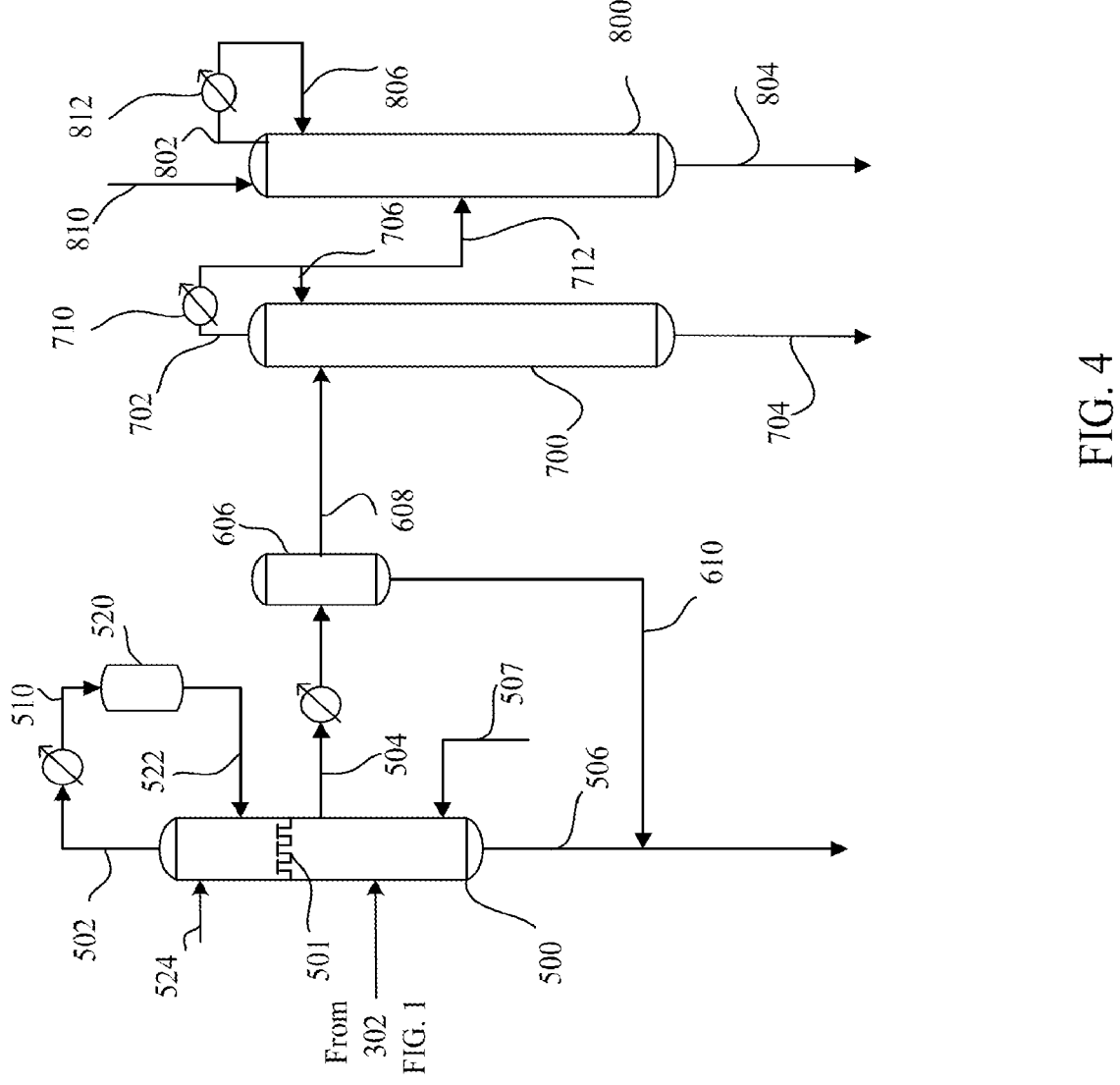
FIG. 4 illustrates a schematic flow diagram of a by-product removal system in accordance with some embodiments of the present invention.
Figure 5:
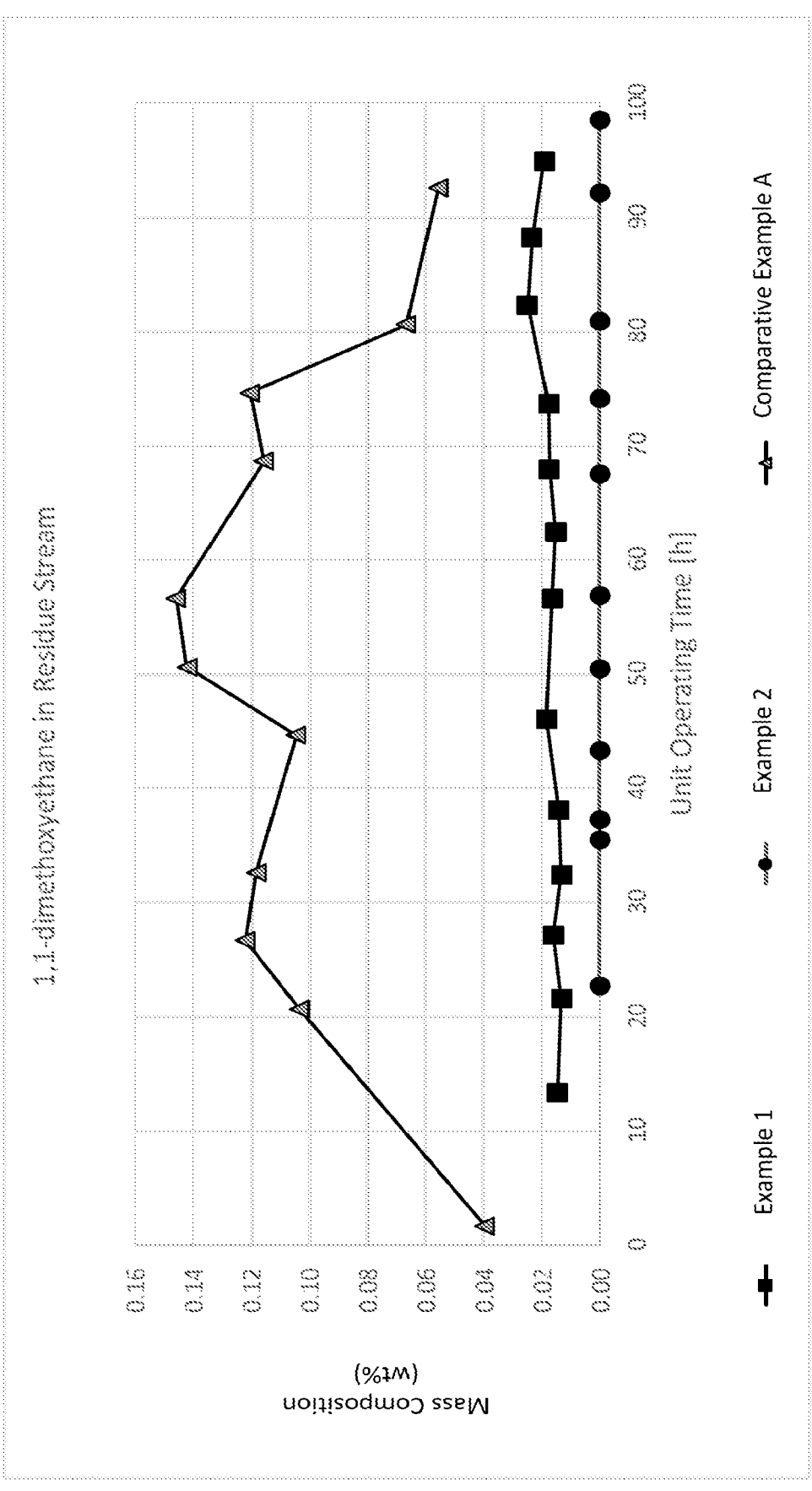
FIG. 5 illustrates a graph of the acetal (1,1-dimethoxyethane) mass composition in the lower stream of the distillation column in accordance with some embodiments of the present invention.

FIG. 4 represents another embodiment that provides a separation process for supplemental acetaldehyde removal process. In one embodiment, the feed stream 302 introduced to the second distillation column 500 includes a portion of the organic phase 404 from the condensed overhead in FIG. 1. Therefore, the feed stream 302 includes $C_1$-$C_{12}$ alkyl iodides (mainly represented by methyl iodide) in an amount from 60 to 98 wt. %, e.g., from 60 to 95 wt. % or from 75 to 93 wt. %, PRC (acetaldehyde) in an amount of up to 5 wt. %, e.g., up to 3 wt. % or up to 0.5 wt. %, and water in an amount up to 3 wt. %, e.g., up to 1 wt. % or up to 0.8 wt. %. Further, feed stream 302 also contains low amounts of methanol, and if the methanol needs to be adjusted, the feed line can further comprise a portion of the aqueous phase 402. As described above, an extractant is added via line 524 above the collector tray 501. Any vapors at the top are collected, condensed and refluxed to the second distillation column 500.

In this embodiment, a sidecut stream 504 is condensed or chilled, from −5° C. to 60° C., for direct feeding to decanter 606, thus skipping vessel 600 in FIG. 3, for liquid-liquid separation to obtain a residual stream 610 (containing methyl iodide) and a liquid stream 608 (containing acetaldehyde). The mass flow ratio of the liquid stream 608 and the residual stream 610 may be from 1:500 to 1:0.5 (liquid to residual), e.g., from 1:400 to 1:1 or from 1:375 to 1:10. The sidecut stream 504 may have a composition that is suitable of phase separation and in one embodiment, the composition of the a sidecut stream 504 may have a PRC mass composition from 0.1 to 90 wt. %, e.g., from 0.2 to 65 wt. % or from 0.5 to 50 wt. %, $C_1$-$C_{12}$ alkyl iodides (methyl iodide) mass composition from 0.5 to 95 wt. %, e.g., from 1 to 95 wt. %, from 5 to 90 wt. %, or from 10 to 60 wt. %, methyl acetate mass composition from 0.1 to 25 wt. %, e.g., from 0.5 to 20 wt. %, or from 0.5 to 10 wt. %, acetic acid mass composition from 0 to 10 wt. %, e.g., from 0.01 to 5 wt. %, or from 0.05 to 1 wt. %, water mass composition from 0.1 to 20 wt. %, e.g., from 0.5 to 15 wt. %, or from 0.5 to 8 wt. %, methanol mass composition from 0 to 2.5 wt. %, e.g., from 0.01 to 2.1 wt. %, or from 0.05 to 2 wt. %, acetal mass composition from 0 to 2.5 wt. %, e.g., from 0.01 to 1.7 wt. %, or from 0.05 to 1.5 wt. %, and dimethyl ether mass composition from 0 to 1.2 wt. %, e.g., from 0.01 to 0.8 wt.

%, or from 0.05 to 0.5 wt. %. The process as shown in FIG. 4 further concentrates the PRC without building up large quantities of acetals.

As shown in FIG. 4, residual stream 610 can be combined with the lower stream 506 from the second distillation column 500. In some embodiments, residual stream 610 may be fed to the lower portion of the second distillation column 500. Acetic acid, as a miscible solvent, was fed via a feed line 507 to the lower portion of second distillation column 500, and may in some embodiments be fed below the feed location of feed stream 302. Although not shown in FIG. 4, there may be a miscible solvent fed to the second distillation column 500.

Once withdrawn from decanter 606, liquid stream 608 is fed to the third distillation column 700. Despite the relatively small stream, the liquid stream 608 contains an useful amount of acetaldehyde. The acetaldehyde mass composition in liquid stream 608 based on amount may be more than 2× the amount in residual stream 610, e.g., more than 3× or more than 4×. As described above, third distillation column 700 operates to yield an third overhead stream 702 containing acetaldehyde in an amount from 1 to 99 wt. % and methyl iodide in an amount from 0.1 to 30 wt. %, and a bottoms stream 704 containing the extractant as the main component in an amount of not less than 10 wt. %, and methyl iodide in an amount of not more than 1 wt. % (provided that, each stream, including impurities, has a total amount of 100% by weight). A portion of the bottoms stream 704 may be used as the extractant and returned to second distillation column 500. In other embodiment, bottoms stream 704 may be removed or discharged from the process.

The overhead stream 704 or a distillate thereof contain more acetaldehyde and has a lower methyl iodide mass composition than second mixture. In one embodiment, the composition of third overhead stream 702 comprises a PRC (acetaldehyde) mass composition from 45 to 99 wt. %, e.g., from 50 to 99 wt. % or from 60 to 98 wt. %, $C_1$-$C_{12}$ alkyl iodides (methyl iodide) mass composition from 0.1 to 30 wt. %, e.g., from 0.5 to 25 wt. %, or from 1 to 20 wt. %, methyl acetate mass composition from 0.1 to 25 wt. %, e.g., from 0.5 to 20 wt. %, or from 0.5 to 12 wt. %, acetic acid mass composition from 0 to 5 wt. %, e.g., from 0 to 1.5 wt. %, or from 0 to 1 wt. %, water mass composition from 0 to 5 wt. %, e.g., from 0 to 2.5 wt. %, or from 0.01 to 2 wt. %, methanol mass composition from 0 to 2.5 wt. %, e.g., from 0.01 to 2.1 wt. %, or from 0.05 to 2 wt. %, acetal mass composition from 0 to 2.5 wt. %, e.g., from 0.01 to 1.7 wt. %, or from 0.05 to 1.5 wt. %, and dimethyl ether mass composition from 0 to 1.2 wt. %, e.g., from 0.01 to 0.8 wt. %, or from 0.05 to 0.5 wt. %. In one embodiment, the third overhead stream 702 has a ratio (based on weight) of methyl iodide relative to acetic acid is that higher than this ratio in feed to the third distillation column 700. In addition or separately, the third overhead stream 702 may have a ratio (based on weight) of methyl iodide relative to methyl acetate is that higher than this ratio in feed to the third distillation column 700. The bottoms stream 704 may have a water mass composition from 85 to 99.99 wt. %, e.g., from 90 to 99.98 wt. % or from 92 to 99 wt. %. In one embodiment, bottoms stream 704 is removed from the process or at least a portion thereof may be returned as the extractant to the second distillation column 500.

Similar to the previous figures, FIG. 4 processes the third overhead stream 702 or a distillate portion thereof, by introducing this stream to the fourth distillation column 800 that operates as an extractive distillation using a water-containing extractive mixture. As described above, fourth distillation column 800 operates in a manner with an water-extracting mixture via line 812 to obtain an fourth overhead stream 802 enriched in methyl iodide and an aqueous bottom stream 804 enriched in acetaldehyde as well as the extractant, being water. At least a portion, including the entire portion, of aqueous bottom stream 804 may be recycled or returned to second distillation column 500 as the extracting mixture.

The material of each member or unit associated with the distillation system, including the columns, valves, condensers, receivers, pumps, reboilers, and internals, and various lines, each communicating to the distillation system may be made of suitable materials such as glass, metal, ceramic, or combinations thereof, and is not particularly limited to a specific one. According to the present invention, the material of the foregoing distillation system and various lines are a transition metal or a transition-metal-based alloy such as iron alloy, e.g., a stainless steel, nickel or nickel alloy, zirconium or zirconium alloy thereof, titanium or titanium alloy thereof, or aluminum alloy. Suitable iron-based alloys include those containing iron as a main component, e.g., a stainless steel that also comprises chromium, nickel, molybdenum and others. Suitable nickel-based alloys include those containing nickel as a main component and one or more of chromium, iron, cobalt, molybdenum, tungsten, manganese, and others, e.g., HASTELLOY™ and INCONEL™. Corrosion-resistant metals may be particularly suitable as materials for the distillation system and various lines.

EXAMPLES

Hereinafter, the present invention will be described in more detail with reference to Examples. However, the present invention is not intended to be limited by these Examples. "MeI" represents methyl iodide, "MA" represents methyl acetate, "MeOH" represents methanol, "DME" represents dimethyl ether, "HOAc" represents acetic acid, and "AcH" represents acetaldehyde.

Example 1

A first mixture was obtained from the organic phase of an overhead decanter on the light ends column using a semi-empirical simulator. The first mixture comprised methanol (1128 ppm). While the majority of the first mixture was methyl iodide and methyl acetate, the first mixture also comprised acetic acid (1.83 wt. %), acetaldehyde (0.186 wt. %), and water (0.7 wt. %). The first mixture was fed to a distillation column having 45 actual stages. The temperature in the lower portion of the distillation column was 46° C. The column operated with a pressure of 1 atm. The column had a collector tray for withdrawing a sidecut stream. An overhead stream was removed, condensed and refluxed. An extracting solvent (water) was added to the upper portion of the distillation. The second mixture was taken from the sidecut stream to further remove acetaldehyde.

In the lower portion of the distillation column, a lower stream was removed. The distillation continued for 100 hours, and sampling was taken periodically to show any changes in the lower stream. The acetal reported in Table 3 is 1,1-dimethoxyethane.

TABLE 3

| Time (hrs) | AcH (Wt. %) | HOAc (Wt. %) | Acetal (Wt. %) | MeOH (Wt. %) | MeAc (Wt. %) | MeI (Wt. %) | Water (Wt. %) |
|---|---|---|---|---|---|---|---|
| 13 | 0.007 | 1.95 | 0.014 | 0.009 | 14.6 | 83.4 | — |
| 22 | 0.002 | 1.95 | 0.014 | 0.003 | 14.5 | 83.6 | — |
| 27 | 0.005 | 2.11 | 0.015 | 0.006 | 15.7 | 82.1 | — |
| 32 | 0.004 | 2.10 | 0.012 | 0.005 | 15.4 | 82.5 | — |
| 38 | 0.005 | 2.50 | 0.014 | 0.005 | 16.8 | 80.7 | — |
| 46 | 0.007 | 1.98 | 0.017 | 0.007 | 14.9 | 83.1 | — |
| 57 | 0.004 | 2.01 | 0.015 | 0.013 | 15.6 | 82.3 | 0.09 |
| 62 | 0.002 | 2.05 | 0.016 | 0.005 | 15.5 | 82.5 | — |
| 68 | 0.004 | 1.97 | 0.016 | 0.007 | 15.2 | 82.7 | 0.04 |
| 74 | 0.002 | 2.12 | 0.016 | 0.006 | 16.1 | 81.7 | 0.03 |
| 88 | 0.005 | 2.13 | 0.022 | 0.010 | 15.8 | 81.9 | 0.09 |
| 95 | 0.004 | 2.12 | 0.018 | 0.006 | 15.5 | 82.4 | — |

The distillation column in Example 1 operated under operating conditions (i) and demonstrated efficiency in yielding a lower stream with very low amounts of 1,1-dimethoxyethane. Thus, acetaldehyde was effectively removed.

In addition to operating conditions (i), Example 1 also met operating conditions (iii) because the acetic acid was greater than the first mixture.

Example 2

Using the same distillation column as Example 1, a first mixture comprising very low amounts of methanol (33 ppm) was used. The first mixture also comprised acetic acid (1.83 wt. %), acetaldehyde (0.196 wt. %), and water (0.31 wt. %), in addition to the methyl iodide and methyl acetate.

In the lower portion of the distillation column, a lower stream was removed. The distillation continued for 100 hours and the changes in the composition is shown below in Table 4. The acetal reported in Table 4 is 1,1-dimethoxyethane.

TABLE 4

Low Methanol in First Mixture

| Time (hrs) | AcH (Wt. %) | HOAc (Wt. %) | Acetal (Wt. %) | MeOH (Wt. %) | MeAc (Wt. %) | MeI (Wt. %) | Water (Wt. %) |
|---|---|---|---|---|---|---|---|
| 23 | 0.024 | 1.84 | — | 0.002 | 14.5 | 68.7 | 0.10 |
| 36 | 0.014 | 2.36 | — | 0.002 | 18.0 | 74.6 | 0.08 |
| 37 | 0.017 | 2.23 | — | 0.002 | 17.2 | 71.5 | 0.09 |
| 43 | 0.017 | 2.76 | — | 0.002 | 20.0 | 77.7 | 0.10 |
| 51 | 0.013 | 2.91 | — | 0.002 | 20.2 | 75.0 | 0.08 |
| 57 | 0.021 | 2.62 | — | 0.002 | 20.3 | 77.1 | 0.13 |
| 68 | 0.019 | 2.17 | — | 0.002 | 17.5 | 67.6 | 0.12 |
| 74 | 0.018 | 2.26 | — | 0.002 | 17.4 | 74.5 | 0.10 |
| 81 | 0.012 | 2.23 | — | 0.002 | 15.5 | 70.1 | 0.06 |

The distillation column in Example 2 operated under operating conditions (i) and demonstrated efficiency in yielding a lower stream and no 1,1-dimethoxyethane was detected. The lower stream was measured for 1,1-dimethoxyethane and the detection limit was 1 ppm. With forming the acetal, the acetaldehyde was effectively removed.

Comparative Example A

To compare with a first mixture containing a high amount of methanol, the same distillation column was used as Example 1. The first mixture comprised methanol in a mass composition of 2.52 wt. %. The first mixture also comprised acetic acid in a mass composition 1.83 wt. %, acetaldehyde in a mass composition 0.2 wt. %, and water in a mass composition 0.71 wt. %, in addition to the methyl iodide and methyl acetate.

Even operating under conditions (i) and (iii), the distillation was unable to maintain the acetal mass composition in the lower stream of less than 0.03 wt. %. This resulted in a loss of acetaldehyde separation efficiency in Table 5.

TABLE 5

Comparative First Mixture

| Time (Hrs) | AcH (Wt. %) | HOAc (Wt. %) | Acetal (Wt. %) | MeOH (Wt. %) | MeAc (Wt. %) | MeI (Wt. %) | Water (Wt. %) |
|---|---|---|---|---|---|---|---|
| 2 | 0.017 | 6.13 | 0.04 | 0.89 | 43.71 | 48.6 | 0.59 |
| 21 | 0.005 | 3.57 | 0.10 | 0.29 | 24.55 | 71.4 | 0.06 |
| 27 | 0.025 | 2.79 | 0.12 | 1.00 | 18.47 | 77.3 | 0.23 |
| 33 | 0.018 | 2.45 | 0.12 | 1.01 | 17.40 | 78.8 | 0.22 |
| 45 | 0.021 | 2.39 | 0.10 | 0.91 | 17.26 | 79.1 | 0.20 |
| 51 | 0.030 | 4.95 | 0.14 | 1.65 | 26.14 | 66.6 | 0.50 |
| 57 | 0.028 | 2.68 | 0.15 | 1.13 | 18.63 | 77.1 | 0.28 |
| 69 | 0.026 | 2.79 | 0.12 | 0.90 | 18.61 | 77.6 | — |
| 75 | 0.025 | 2.68 | 0.12 | 0.91 | 18.10 | 77.9 | 0.21 |
| 81 | 0.015 | 2.68 | 0.07 | 0.14 | 17.81 | 79.2 | 0.05 |
| 93 | 0.013 | 2.77 | 0.06 | 0.16 | 18.23 | 78.7 | 0.06 |

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

Embodiments

As used below, any reference to a series of embodiments is to be understood as a reference to each of those embodiments disjunctively (e.g., "Embodiments 1-4" is to be understood as "Embodiments 1, 2, 3, or 4").

Embodiment 1 is a process for separating acetaldehyde from a first mixture comprising acetaldehyde, one or more $C_1$-$C_{12}$ alkyl iodides, water, and methanol, the process comprising the steps of: distilling the first mixture in a distillation column to form at least two streams selected from the group consisting of an overhead stream, sidecut stream, and lower stream, wherein either the overhead stream or sidecut stream are withdrawn as a second mixture; separating acetaldehyde from the second mixture; and controlling the 1,1-dimethoxyethane mass composition in the lower stream to less than or equal to 0.03 wt. % by operating the distillation column under at least one of the following conditions (i) to (iii): (i) temperature in a lower portion of the distillation column is not less than 40° C.; (ii) water mass composition in the lower stream is not less than 0.3 wt. %; or (iii) acetic acid mass composition in the lower stream on weight percentage basis is greater than the acetic acid mass composition in the first mixture; and wherein the methanol mass composition in the first mixture is less than or equal to 2 wt. %.

Embodiment 2 is the process of embodiment(s) 1, wherein the methanol mass composition in the first mixture is less than or equal to 1 wt. %.

Embodiment 3 is the process of embodiment(s) 1-2, wherein the methanol mass composition in the first mixture is less than or equal to 0.5 wt. %.

Embodiment 4 is the process of embodiment(s) 1-3, wherein the pressure in the distillation column is from 0.1 to 0.7 MPa.

Embodiment 5 is the process of embodiment(s) 1-4, wherein the weight ratio of 1,1-dimethoxyethane mass composition in the lower stream to overhead stream is 100:1 to 10:1.

Embodiment 6 is the process of embodiment(s) 1-5, wherein the weight ratio of 1,1-dimethoxyethane mass composition in the lower stream to sidecut stream is 100:1 to 10:1.

Embodiment 7 is the process of embodiment(s) 1-6, wherein the second mixture comprises a portion of the overhead stream and a portion of the sidecut.

Embodiment 8 is the process of embodiment(s) 1-7, wherein the step of separating acetaldehyde from the second mixture further comprises feeding at least a portion of second mixture to a vessel under conditions sufficient to phase separate the second mixture into an aqueous phase and an organic phase.

Embodiment 9 is the process of embodiment(s) 8, wherein the organic phase is fed to the lower portion of distillation column under the at least one of the conditions (i) to (iii).

Embodiment 10 is the process of embodiment(s) 8-9, wherein the organic phase comprises methanol, and the total methanol mass composition in the organic phase and first mixture is less than or equal to 2 wt. %.

Embodiment 11 is the process of embodiment(s) 1-10, wherein the distillation column for distilling the first mixture is an extractive distillation step and further comprising adding an extractant to an upper portion of the distillation column.

Embodiment 12 is the process of embodiment(s) 1-11, wherein for condition (ii) the water mass composition in the lower stream is not less than 0.6 wt. %.

Embodiment 13 is the process of embodiment(s) 1-12, wherein for condition (iii) the acetic acid mass composition in the lower stream is not more than 3 wt. %.

Embodiment 14 is the process of embodiment(s) 1-13, wherein the distillation column has more than 10 stages.

Embodiment 15 is the process of embodiment(s) 1-14, wherein the reflux ratio of the distillation column is from 1:20 to 20:1.

Embodiment 16 is the process of embodiment(s) 1-15, wherein the first mixture comprises acetaldehyde in a mass composition from 0.01 to 30 wt. %, one or more $C_1$-$C_{12}$ alkyl iodides in a mass composition from 0.1 to 90 wt. %, water in a mass composition from 0.1 to 90 wt. %, and methanol in a mass composition from 0.001 to 2 wt. %, based on the total weight of the first mixture.

Embodiment 17 is the process of embodiment(s) 1-16, wherein the methanol mass composition in the first mixture is more than the dimethyl ether mass composition.

Embodiment 18 is the process of embodiment(s) 1-17, wherein the distillation column is operated under conditions to prevent formation of methanol.

Embodiment 19 is a process for separating acetaldehyde from a first mixture comprising acetaldehyde, one or more $C_1$-$C_{12}$ alkyl iodides, water, and methanol, the process comprising the steps of: distilling the first mixture in a distillation column to form at least two streams selected from the group consisting of an overhead stream, sidecut stream, and lower stream, wherein the sidecut stream is withdrawn as a second mixture; separating the second mixture into an aqueous stream comprising acetaldehyde or an organic stream comprising the one or more $C_1$-$C_{12}$ alkyl iodides; and controlling the 1,1-dimethoxyethane mass composition in the lower stream to less than or equal to 0.03 wt. % by operating the distillation column under at least one of the following conditions (i) to (iii): (i) temperature in a lower portion of the distillation column is not less than 40° C.; (ii) water mass composition in the lower stream is not less than 0.3 wt. %; or (iii) acetic acid mass composition in the lower stream on weight percentage basis is greater than the acetic acid mass composition in the first mixture; and wherein the methanol mass composition in the first mixture is less than or equal to 2 wt. %.

Embodiment 20 is the process of embodiment(s) 19, wherein the distillation column for distilling the first mixture is an extractive distillation step and further comprising adding an extractant to an upper portion of the distillation column.

We claim:

1. A process for separating acetaldehyde from a first mixture comprising acetaldehyde, one or more C1-C12 alkyl iodides, water, and methanol, the process comprising the steps of:

distilling the first mixture in a distillation column to form at least two streams selected from the group consisting of an overhead stream, sidecut stream, and lower stream, wherein either the overhead stream or sidecut stream are withdrawn as a second mixture;

separating acetaldehyde from the second mixture; and controlling a 1,1-dimethoxyethane mass composition in the lower stream to less than or equal to 0.03 wt. % by operating the distillation column under at least one of the following conditions (i) to (iii):

(i) temperature in a lower portion of the distillation column is not less than 40° C.;

(ii) water mass composition in the lower stream is not less than 0.3 wt. %; or (iii) acetic acid mass composition in the lower stream on weight percentage basis is greater than the acetic acid mass composition in the first mixture;

wherein a methanol mass composition in the first mixture is less than or equal to 2 wt. %; and wherein the water to acetic acid ratio in the lower stream is from 1:10 to 1:100.

2. The process of claim 1, wherein the methanol mass composition in the first mixture is less than or equal to 1 wt. %.

3. The process of claim 1, wherein the methanol mass composition in the first mixture is less than or equal to 0.5 wt. %.

4. The process of claim 1, wherein the pressure in the distillation column is from 0.1 to 0.7 MPa.

5. The process of claim 1, wherein the weight ratio of 1,1-dimethoxyethane mass composition in the lower stream to overhead stream is 100:1 to 10:1.

6. The process of claim 1, wherein the weight ratio of 1,1-dimethoxyethane mass composition in the lower stream to sidecut stream is 100:1 to 10:1.

7. The process of claim 1, wherein the second mixture comprises a portion of the overhead stream and a portion of the sidecut.

8. The process of claim 1, wherein the step of separating acetaldehyde from the second mixture further comprises feeding at least a portion of second mixture to a vessel under conditions sufficient to phase separate the second mixture into an aqueous phase and an organic phase.

9. The process of claim 8, wherein the organic phase is fed to the lower portion of distillation column under the at least one of the conditions (i) to (iii).

10. The process of claim 8, wherein the organic phase comprises methanol, and the total methanol mass composition in the organic phase and first mixture is less than or equal to 2 wt. %.

11. The process of claim 1, wherein the distillation column for distilling the first mixture is an extractive distillation step and further comprising adding an extractant to an upper portion of the distillation column.

12. The process of claim 1, wherein for condition (ii) the water mass composition in the lower stream is not less than 0.6 wt. %.

13. The process of claim 1, wherein for condition (iii) the acetic acid mass composition in the lower stream is not more than 3 wt. %.

14. The process of claim 1, wherein the distillation column has more than 10 stages.

15. The process of claim 1, wherein the reflux ratio of the distillation column is from 1:20 to 20:1.

16. The process of claim 1, wherein the first mixture comprises acetaldehyde in a mass composition from 0.01 to 30 wt. %, one or more C1-C12 alkyl iodides in a mass composition from 0.1 to 90 wt. %, water in a mass composition from 0.1 to 90 wt. %, and methanol in a mass composition from 0.001 to 2 wt. %, based on the total weight of the first mixture.

17. The process of claim 1, wherein the methanol mass composition in the first mixture is more than a dimethyl ether mass composition.

18. The process of claim 1, wherein the distillation column is operated under conditions to prevent formation of methanol.

19. A process for separating acetaldehyde from a first mixture comprising acetaldehyde, one or more C1-C12 alkyl iodides, water, and methanol, the process comprising the steps of:

distilling the first mixture in a distillation column to form at least two streams selected from the group consisting of an overhead stream, sidecut stream, and lower stream, wherein the sidecut stream is withdrawn as a second mixture;

separating the second mixture into an aqueous stream comprising acetaldehyde or an organic stream comprising the one or more C1-C12 alkyl iodides; and controlling a 1,1-dimethoxyethane mass composition in the lower stream to less than or equal to 0.03 wt. % by operating the distillation column under at least one of the following conditions (i) to (iii):

(i) temperature in a lower portion of the distillation column is not less than 40° C.;

(ii) water mass composition in the lower stream is not less than 0.3 wt. %; or (iii) acetic acid mass composition in the lower stream on weight percentage basis is greater than the acetic acid mass composition in the first mixture;

wherein the water to acetic acid ratio in the lower stream is from 1:10 to 1:100; and wherein a methanol mass composition in the first mixture is less than or equal to 2 wt. %.

20. The process of claim 19, wherein the distillation column for distilling the first mixture is an extractive distillation step and further comprising adding an extractant to an upper portion of the distillation column.

* * * * *